(12) United States Patent
Kelly et al.

(10) Patent No.: US 12,221,425 B2
(45) Date of Patent: Feb. 11, 2025

(54) PROCESS FOR THE PREPARATION OF CIC-1 CHLORIDE CHANNEL INHIBITORS

(71) Applicant: NMD PHARMA A/S, Aarhus (DK)

(72) Inventors: Nicholas Kelly, Bagsværd (DK); Michael John McKenzie, Leicester (GB)

(73) Assignee: NMD PHARMA A/S, Aarhus N (DK)

( * ) Notice: Subject to any disclaimer, the term of this patent is extended or adjusted under 35 U.S.C. 154(b) by 571 days.

(21) Appl. No.: 17/619,312

(22) PCT Filed: Jun. 19, 2020

(86) PCT No.: PCT/EP2020/067065
§ 371 (c)(1),
(2) Date: Dec. 15, 2021

(87) PCT Pub. No.: WO2020/254554
PCT Pub. Date: Dec. 24, 2020

(65) Prior Publication Data
US 2022/0298124 A1 Sep. 22, 2022

(30) Foreign Application Priority Data
Jun. 19, 2019 (EP) .................................... 19181262

(51) Int. Cl.
*C07D 261/08* (2006.01)
(52) U.S. Cl.
CPC .................................. *C07D 261/08* (2013.01)

(58) Field of Classification Search
CPC .................................................... C07D 261/08
See application file for complete search history.

(56) References Cited

U.S. PATENT DOCUMENTS 10,385,028 B2 * 8/2019 Knutsen ............... C07D 213/30

FOREIGN PATENT DOCUMENTS

| WO | 2016202341 A1 | 12/2016 |
| WO | 2019115781 A1 | 6/2019 |

OTHER PUBLICATIONS

International Search Report (PCT/ISA/210) and Written Opinion (PCT/ISA/237) mailed on Jul. 28, 2020, by the European Patent Office as the International Searching Authority for International Application No. PCT/EP2020/067065. (12 pages).

Ito, Shoei, et al., "A Simple Synthetic Method of trans-5-Aryl and 5-Cyclopropyl Derivatives of 2-Isoxazolin-4-ol via Intramolecular Ring Opening of α,β-Epoxy Ketone Oximes".

* cited by examiner

*Primary Examiner* — Timothy R Rozof
(74) *Attorney, Agent, or Firm* — BUCHANAN INGERSOLL & ROONEY PC

(57) ABSTRACT

This disclosure relates to an improved chemical process for making compounds which are CIC-1 chloride channel inhibitors.

22 Claims, 3 Drawing Sheets

A

B

A

B

PROCESS FOR THE PREPARATION OF CIC-1 CHLORIDE CHANNEL INHIBITORS

TECHNICAL FIELD

The present disclosure relates to novel chemical processes for the synthesis of CIC-1 chloride channel inhibitors.

BACKGROUND

This disclosure relates to chemical processes for making compounds which are CIC-1 chloride channel inhibitors. As described in WO 2016/202341, CIC-1 chloride channel inhibitors may be useful in the treatment of neuromuscular disorders, such as myasthenia gravis and ALS, or in reversing and/or ameliorating a neuromuscular blockade.

SUMMARY

In order to develop treatments of neuromuscular disorders, there is a need for CIC-1 chloride channel inhibitors. The present disclosure provides a novel industrially applicable process for the preparation of compounds of Formula I. The compounds of Formula I inhibit CIC-1 ion channels and are capable of restoring neuromuscular transmission, as evidenced by the data generated by investigation of the compound set in biological models described herein. These compounds can thus be used to treat or ameliorate muscle weakness and muscle fatigue in neuromuscular junction disorders caused by disease or by neuromuscular blocking agents.

In one aspect, the disclosure provides a process for the preparation of compounds of Formula I

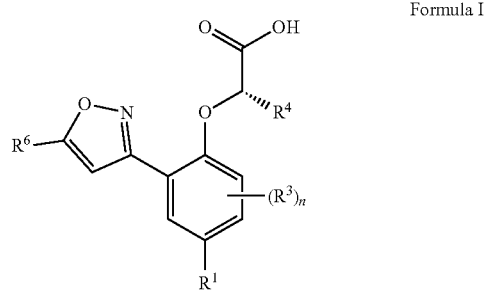

Formula I comprising step a) wherein
i) a compound of Formula II is reacted with an acid or base

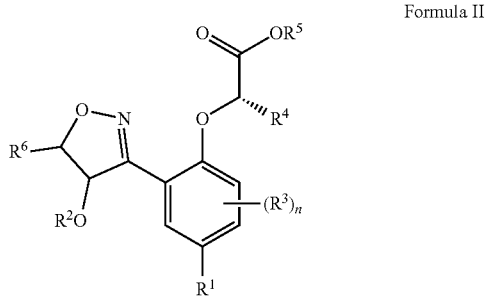

Formula II and
ii) a compound of Formula I is isolated from the reaction mixture,
wherein $R^1$ to $R^9$ and n are as defined herein.
The disclosure further relates to novel compounds of Formula II as defined herein.

DESCRIPTION OF DRAWINGS

FIG. 3 shows representative plots of normalized instant tail currents from a CIC-1 expressing CHO cell patch before (circles) and after (squares) application of 100 μM 9-AC. The instant tail currents at each voltage step were normalized to the maximal tail current obtained following the (+)120 mV voltage step and fitted to a Boltzmann function to determine the half activation potential, $V_{1/2}$.

DEFINITIONS

Figure 1:
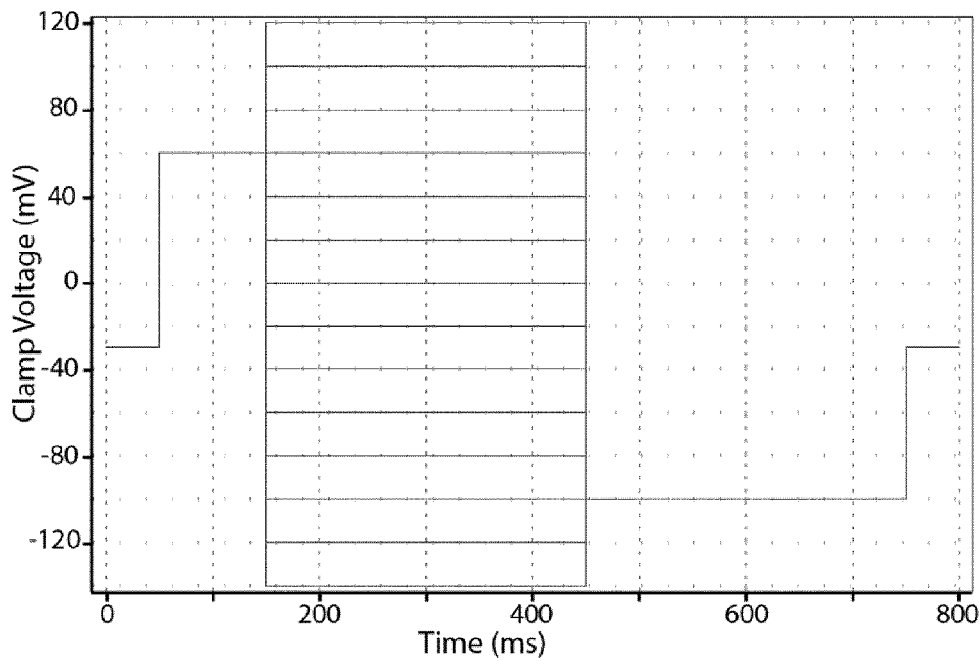
FIG. 1: Panel A illustrates the voltage protocol used to evoke currents in whole cell patches of CHO cells expressing human CIC-1 channels. Panel B shows representative whole cell current traces from a patched CHO cell expressing human CIC-1 channels. Currents were evoked by applying the voltage protocol shown in Panel A.
Figure 1:
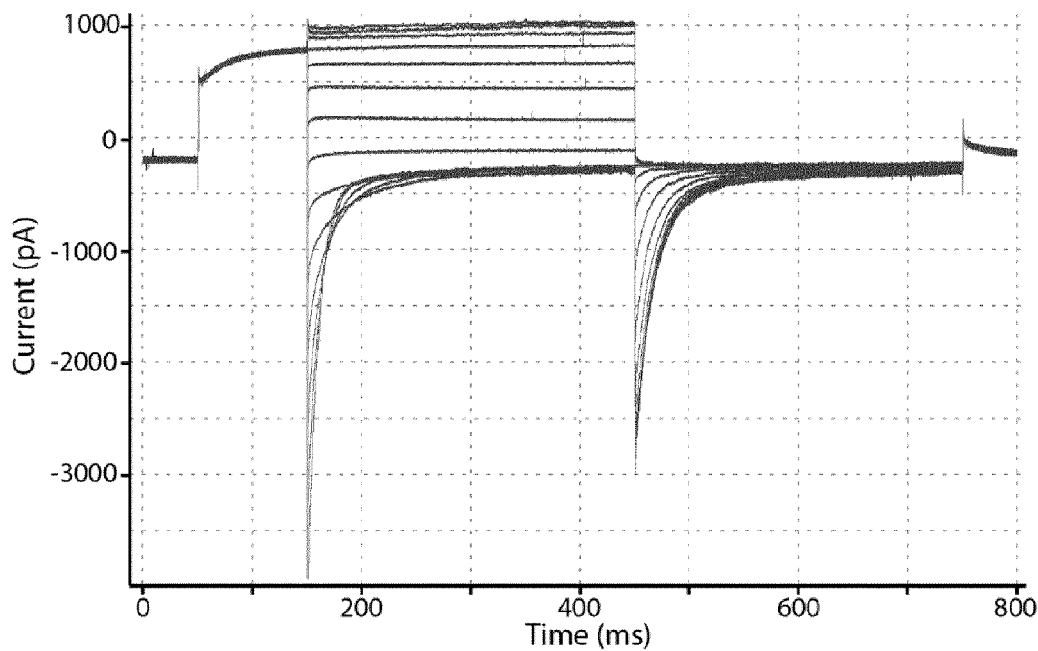

The terms "$C_{1-3}$ alkyl" and "$C_{1-5}$ alkyl" refers to a branched or unbranched alkyl group having from one to three or one to five carbon atoms respectively, including but not limited to methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.

The term "$C_{2-5}$ alkenyl" refers to a branched or unbranched alkenyl group having from two to five carbon atoms, two of which are connected by a double bond, including but not limited to ethenyl, propenyl, isopropenyl, butenyl, isobutenyl, pentenyl and isopentenyl.

The term "$C_{2-5}$ alkynyl" refers to a branched or unbranched alkynyl group having from two to five carbon atoms, two of which are connected by a triple bond, including but not limited to ethynyl, prop-1-ynyl, prop-2-ynyl, but-1-ynyl, but-2-ynyl, but-3-ynyl, buta-1,3-diynyl, pent-1-ynyl, pent-2-ynyl, pent-3-ynyl, pent-4-ynyl, penta-2,4-diynyl and penta-1,3-diynyl.

The term "$C_{3-5}$ cycloalkyl" and "$C_{3-6}$ cycloalkyl" refers to a group having three to five or three to six carbon atoms respectively including a monocyclic or bicyclic carbocycle, including but not limited to cyclopropyl, cyclobutyl, cyclopentyl and cyclohexyl.

DETAILED DESCRIPTION

The present disclosure provides a novel industrially applicable process for the preparation of compounds of Formula I which are CIC-1 chloride channel inhibitors.

The present process allows for better control of impurities, reduces or removes the need for chromatographic steps and has higher yields thereby providing better cost of goods.

Thus, in one aspect, the disclosure provides a process for the preparation of compounds of Formula I

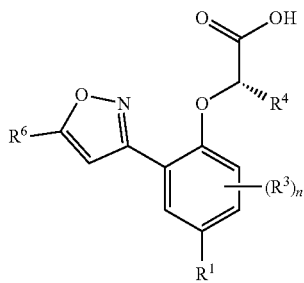

Formula I comprising step a) wherein
i) a compound of Formula II is reacted with an acid or base

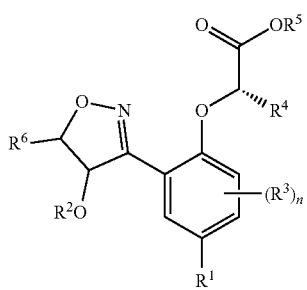

Formula II and
ii) a compound of Formula I is isolated from the reaction mixture,
wherein
$R^1$ is selected from the group consisting of H, F, Cl, Br and I;
$R^2$ is selected from the group consisting of $C_{1-5}$ alkyl and $C_{3-5}$ cycloalkyl;
$R^3$ is selected from the group consisting of deuterium, F, Cl, Br and I;
$R^4$ is selected from the group consisting of H, deuterium, $C_{1-5}$ alkyl, $C_{2-5}$ alkenyl, $C_{2-5}$ alkynyl, $C_{3-5}$ cycloalkyl and $C_5$ cycloalkenyl, each of which may be optionally substituted with one or more, identical or different, substituents $R^1$;
$R^5$ is selected from the group consisting of $C_{1-5}$ alkyl optionally substituted with one or more, identical or different, substituents $R^8$, $C_{2-5}$ alkenyl, $C_{2-5}$ alkynyl, $C_{3-6}$ cycloalkyl optionally substituted with one or more, identical or different, substituents $R^8$, phenyl optionally substituted with one or more, identical or different, substituents $R^9$ and benzyl optionally substituted with one or more, identical or different, substituents $R^9$;
$R^6$ is selected from the group consisting of H, deuterium $C_{1-5}$ alkyl and $C_{3-5}$ cycloalkyl;
$R^7$ is independently selected from the group consisting of deuterium, tritium, F, Cl, Br, I, CN, isocyanide, $C_{3-5}$ cycloalkyl optionally substituted with one or more, identical or different, substituents $R^8$, O—$C_{1-3}$ alkyl optionally substituted with one or more, identical or different, substituents $R^8$, S—$C_{1-3}$ alkyl optionally substituted with one or more, identical or different, substituents $R^8$, $CH_2$—O—$C_{1-3}$ alkyl optionally substituted with one or more, identical or different, substituents $R^8$ and $CH_2$—S—$C_{1-3}$ alkyl optionally substituted with one or more, identical or different, substituents $R^8$;
$R^8$ is independently selected from the group consisting of deuterium and F;
$R^9$ is independently selected from the group consisting of deuterium, methoxy, nitro, cyano, Cl, Br, I and F; and
n is an integer 0, 1, 2 or 3.

In one embodiment, $R^1$ is Cl or Br. In one embodiment, $R^1$ is Cl. In one embodiment, $R^1$ is Br.

In one embodiment, $R^2$ is $C_{1-5}$ alkyl. In one embodiment, $R^2$ is selected from the group consisting of methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl. In one embodiment, $R^2$ is ethyl. In one embodiment, $R^2$ is prop-1-yl. In one embodiment, $R^2$ is prop-2-yl. In one embodiment, $R^2$ is but-1-yl. In one embodiment, $R^2$ is 2-methyl-prop-2-yl.

In one embodiment, $R^3$ is deuterium. In one embodiment, $R^3$ is F.

In one embodiment, $R^4$ is H. In one embodiment, $R^4$ is $C_{1-5}$ alkyl optionally substituted with one or more, identical or different, substituents $R^7$. In one embodiment, $R^4$ is $C_{1-5}$ alkyl substituted with $C_{3-5}$ cycloalkyl optionally substituted with one or more, identical or different, substituents $R^8$. In one embodiment, $R^4$ is Me. In one embodiment, $R^4$ is Et. In one embodiment, $R^4$ is —$CH_2F$. In one embodiment, $R^5$ is cyclopropyl.

In one embodiment, $R^5$ is $C_{1-5}$ alkyl optionally substituted with one or more, identical or different, substituents $R^8$. In one embodiment, $R^5$ is Me. In one embodiment, $R^5$ is Et.

In one embodiment, $R^5$ is 2-methyl-prop-2-yl.

In one embodiment, $R^6$ is H. In one embodiment, $R^6$ is deuterium. In one embodiment, $R^6$ is $C_{1-5}$ alkyl. In one embodiment, $R^6$ is selected from the group consisting of methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.

In one embodiment, $R^7$ is deuterium. In one embodiment, $R^7$ is F. In one embodiment, $R^7$ is $C_{3-5}$ cycloalkyl optionally substituted with one or more, identical or different, substituents $R^8$. In one embodiment, $R^4$ is $C_{1-5}$ alkyl substituted with $R^7$, wherein $R^7$ is $C_{3-5}$ cycloalkyl optionally substituted with one or more, identical or different, substituents $R^8$.

In one embodiment, n is 0. In one embodiment, n is 1. In one embodiment, n is 2. In one embodiment, n is 3.

In one embodiment the compound of Formula II is reacted with an acid. In one embodiment the compound of Formula II is reacted with a concentrated acid. In one embodiment the compound of Formula II is reacted with an acid selected from the group formic acid, acetic acid, propionic acid, butyric acid, benzoic acid, hydrochloric acid and sulfuric acid or a mixture thereof, such as a mixture of formic acid and acetic acid. In one embodiment the acid is acetic acid. In one embodiment, the acid is formic acid. In one embodiment, the acid is concentrated acetic acid. In one embodiment, the acid is concentrated formic acid. In one embodiment, the acid is concentrated acetic acid. In one embodiment, the acid is a mixture of concentrated formic acid and concentrated acetic acid.

In one embodiment, step a) i) is performed at a temperature of between 70° C. and 140° C., such as between 80° C. and 130° C., for example between 90° C. and 120° C.

In one embodiment, the reaction time of step a) i) is between 12 hours and 96 hours, such as between 24 and 72 hours, for example between 36 and 60 hours.

In one embodiment, the amount of acid used in step a) i) is between 3 mL per gram of starting material and 15 mL per gram of starting material.

In one embodiment, the compound of Formula I is isolated from the reaction mixture by adding water and extracting the product into an organic solvent. In one embodiment, the organic solvent used for the extraction is selected from the list consisting of toluene, ethyl acetate, isopropyl acetate and tert-butyl methyl ether. In one embodiment, the organic solvent used for the extraction is tert-butyl methyl ether.

In one embodiment, the compound of Formula I is purified by crystallisation from an organic solvent is selected from the list consisting of toluene, ethyl acetate, isopropyl acetate and tert-butyl methyl ether. In one embodiment, the compound of Formula I is purified by crystallisation from toluene.

In one embodiment, the process further comprises step b) wherein i) a compound of Formula III

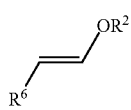

Formula III is reacted with N-chlorosuccinimide in an organic solvent;

ii) a compound of Formula IV

Formula IV and a base are added to the reaction mixture; and iii) a compound of Formula II is isolated from the reaction mixture, wherein $R^1$ to $R^9$ and n are as defined herein.

In one embodiment, the solvent in step b) i) is dimethylformamide (DMF). In one embodiment, the compound of formula IV is selected from the group consisting of ethyl vinyl ether, n-butyl vinyl ether and tert-butyl vinyl ether. In one embodiment, the compound of formula IV is n-butyl vinyl ether. In one embodiment, the base in step b) ii) is a trialkylamine. In one embodiment, the base in step b) ii) is selected from the group consisting of trimethylamine, triethylamine, triisopropylamine and N,N-diisopropylethylamine. In one embodiment, the base in step b) ii) is triethylamine.

In one embodiment, the process further comprises step c) wherein i) a compound of Formula V

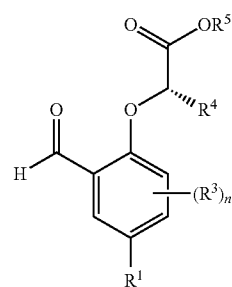

Formula V is reacted with hydroxylamine in an organic solvent;

ii) a base is added to the reaction mixture; and iii) a compound of Formula III is isolated from the reaction mixture, wherein $R^1$ to $R^9$ and n are as defined herein.

In one embodiment, the process further comprises step d) wherein i) a compound of Formula VI

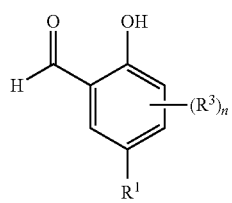

Formula VI is added to a compound of Formula VII in an organic solvent;

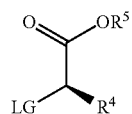

Formula VI ii) a base is added to the reaction mixture; and iii) a compound of Formula V is isolated from the reaction mixture, wherein $R^1$ to $R^9$ and n are as defined herein and LG is a leaving group.

In one embodiment, the leaving group is selected from the group consisting of tosylate, mesylate, triflate, nosylate, brosylate, bromide, iodide and chloride.

In one embodiment, the process comprises step a) as outlined in Scheme 1. In one embodiment, the process comprises steps a) and b) as outlined in Scheme 1. In one embodiment, the process comprises steps a), b) and c) as outlined in Scheme 1. In one embodiment, the process comprises steps a), b), c), and d) as outlined in Scheme 1.

Scheme 1 Synthesis of compounds of Formula I

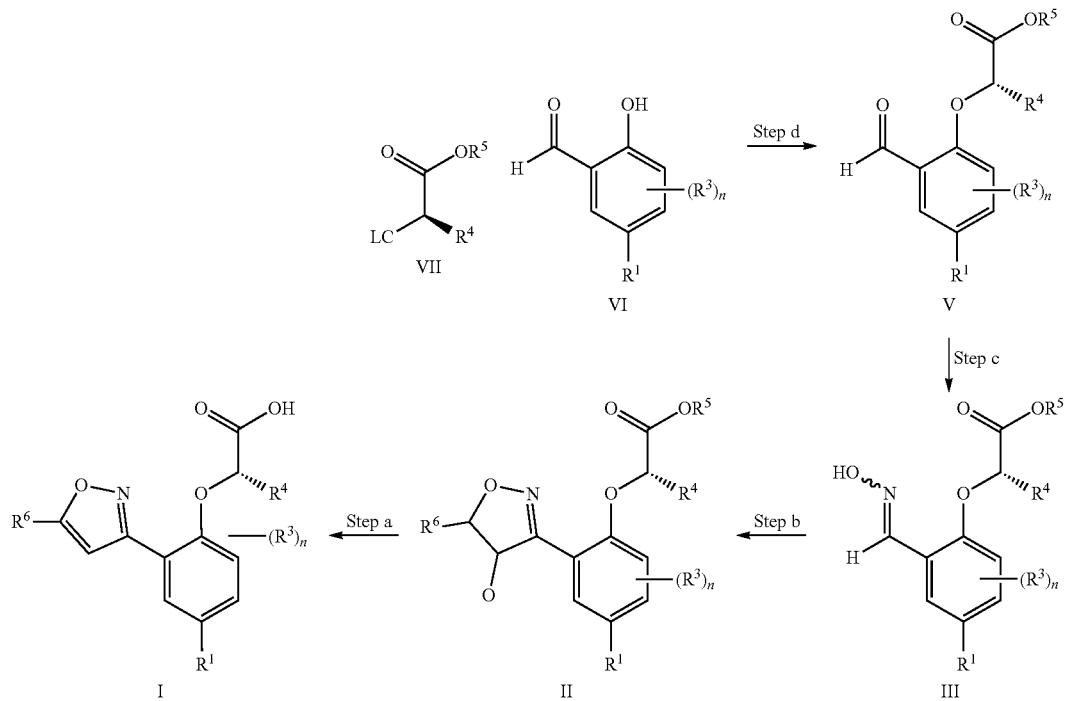

In one embodiment, the compound of Formula I is an inhibitor of the ClC-1 chloride ion channel.

In one embodiment, the compound of Formula I is at least 80% pure, such as at least 90% pure, such as at least 95% pure, such as at least 96% pure, such as at least 97% pure, such as at least 98% pure.

In certain embodiments, the compound or the compound for use according to the present disclosure can have >90% enantiomeric excess. In certain embodiments, the compound or the compound for use according to the present disclosure can have >95% e.e.

In one embodiment, the compound of Formula I is selected from the group consisting of:
(2S)-2-[4-bromo-5-fluoro-2-(1,2-oxazol-3-yl)phenoxy]-2-cyclopropylacetic acid;
(2S)-2-[4-bromo-2-(1,2-oxazol-3-yl)phenoxy]-3-cyclobutylpropanoic acid;
2-[4-bromo-5-fluoro-2-(1,2-oxazol-3-yl)phenoxy]acetic acid;
2-[4-bromo-2-(1,2-oxazol-3-yl)phenoxy]acetic acid;
(2S)-2-[4,5-dichloro-2-(1,2-oxazol-3-yl)phenoxy]propanoic acid;
(2S)-2-[4-bromo-5-fluoro-2-(1,2-oxazol-3-yl)phenoxy]propanoic acid;
(2S)-2-[4-chloro-5-fluoro-2-(1,2-oxazol-3-yl)phenoxy]propanoic acid;
(2S)-2-[4-chloro-2-(1,2-oxazol-3-yl)phenoxy]-3-cyclopropylpropanoic acid;
(2S)-2-[4-fluoro-2-(1,2-oxazol-3-yl)phenoxy]propanoic acid;
(2 S)-2-[4-chloro-2-(5-cyclopropyl-1,2-oxazol-3-yl)phenoxy]propanoic acid;
(2S)-2-[4-chloro-2-(1,2-oxazol-3-yl)phenoxy]-3-methylbutanoic acid;
(2S)-2-[4-chloro-2-(1,2-oxazol-3-yl)phenoxy]butanoic acid;
(2S)-2-[4-chloro-2-(1,2-oxazol-3-yl)phenoxy]propanoic acid;
(2S)-2-[4-bromo-2-(1,2-oxazol-3-yl)phenoxy]-3-cyclopropylpropanoic acid;
(2S)-2-[4-bromo-2-(1,2-oxazol-3-yl)phenoxy]butanoic acid;
(2S)-2-[4-bromo-2-(1,2-oxazol-3-yl)phenoxy]-3-methylbutanoic acid;
(2 S)-2-[4-bromo-2-(5-methyl-1,2-oxazol-3-yl)phenoxy] propanoic acid;
(2S)-2-[4-bromo-2-(5-cyclopropyl-1,2-oxazol-3-yl)phenoxy]propanoic acid; and
(2S)-2-[4-bromo-2-(1,2-oxazol-3-yl)phenoxy]propanoic acid.

In one aspect, the disclosure relates to a process for the preparation of a pharmaceutical composition comprising the steps of:
i) preparing a compound selected from the group consisting of
(2S)-2-[4-bromo-5-fluoro-2-(1,2-oxazol-3-yl)phenoxy]-2-cyclopropylacetic acid;
(2S)-2-[4-bromo-2-(1,2-oxazol-3-yl)phenoxy]-3-cyclobutylpropanoic acid;
2-[4-bromo-5-fluoro-2-(1,2-oxazol-3-yl)phenoxy]acetic acid;
2-[4-bromo-2-(1,2-oxazol-3-yl)phenoxy]acetic acid;
(2S)-2-[4,5-dichloro-2-(1,2-oxazol-3-yl)phenoxy]propanoic acid;
(2 S)-2-[4-bromo-5-fluoro-2-(1,2-oxazol-3-yl)phenoxy]propanoic acid;
(2S)-2-[4-chloro-5-fluoro-2-(1,2-oxazol-3-yl)phenoxy]propanoic acid;
(2S)-2-[4-chloro-2-(1,2-oxazol-3-yl)phenoxy]-3-cyclopropylpropanoic acid;
(2S)-2-[4-fluoro-2-(1,2-oxazol-3-yl)phenoxy]propanoic acid;

(2S)-2-[4-chloro-2-(5-cyclopropyl-1,2-oxazol-3-yl)phenoxy]propanoic acid;
(2S)-2-[4-chloro-2-(1,2-oxazol-3-yl)phenoxy]-3-methylbutanoic acid;
(2S)-2-[4-chloro-2-(1,2-oxazol-3-yl)phenoxy]butanoic acid;
(2S)-2-[4-chloro-2-(1,2-oxazol-3-yl)phenoxy]propanoic acid;
(2S)-2-[4-bromo-2-(1,2-oxazol-3-yl)phenoxy]-3-cyclopropylpropanoic acid;
(2S)-2-[4-bromo-2-(1,2-oxazol-3-yl)phenoxy]butanoic acid;
(2 S)-2-[4-bromo-2-(1,2-oxazol-3-yl)phenoxy]-3-methylbutanoic acid;
(2S)-2-[4-bromo-2-(5-methyl-1,2-oxazol-3-yl)phenoxy]propanoic acid;
(2S)-2-[4-bromo-2-(5-cyclopropyl-1,2-oxazol-3-yl)phenoxy]propanoic acid; and
(2 S)-2-[4-bromo-2-(1,2-oxazol-3-yl)phenoxy]propanoic acid according to the present invention; and
ii) formulating said compound into a pharmaceutical composition.

In one aspect, the present disclosure is directed to a compound of Formula II as defined herein.

In one embodiment, the compound of Formula II is selected from the group consisting of:
methyl (2S)-2-[4-bromo-2-(4-butoxy-4,5-dihydroisoxazol-3-yl)phenoxy]propanoate;
ethyl (2S)-2-[4-bromo-2-(4-butoxy-4,5-dihydroisoxazol-3-yl)phenoxy]propanoate;
tert-butyl (2S)-2-[4-bromo-2-(4-butoxy-4,5-dihydroisoxazol-3-yl)phenoxy]propanoate;
methyl (2S)-2-[4-bromo-2-(4-ethoxy-4,5-dihydroisoxazol-3-yl)phenoxy]propanoate;
ethyl (2S)-2-[4-bromo-2-(4-ethoxy-4,5-dihydroisoxazol-3-yl)phenoxy]propanoate;
tert-butyl (2S)-2-[4-bromo-2-(4-ethoxy-4,5-dihydroisoxazol-3-yl)phenoxy]propanoate;
methyl (2S)-2-[4-chloro-2-(5-cyclopropyl-4-butoxy-4,5-dihydroisoxazol-3-yl)phenoxy]propanoate;
methyl (2S)-2-[4-bromo-2-(5-methyl-4-butoxy-4,5-dihydroisoxazol-3-yl)phenoxy]propanoate;
methyl (2S)-2-[4-bromo-2-(5-cyclopropyl-4-butoxy-4,5-dihydroisoxazol-3-yl)phenoxy]propanoate;
ethyl (2S)-2-[4-chloro-2-(5-cyclopropyl-4-butoxy-4,5-dihydroisoxazol-3-yl)phenoxy]propanoate;
ethyl (2S)-2-[4-bromo-2-(5-methyl-4-butoxy-4,5-dihydroisoxazol-3-yl)phenoxy]propanoate;
ethyl (2S)-2-[4-bromo-2-(5-cyclopropyl-4-butoxy-4,5-dihydroisoxazol-3-yl)phenoxy]propanoate;
tert-butyl (2S)-2-[4-chloro-2-(5-cyclopropyl-4-butoxy-4,5-dihydroisoxazol-3-yl)phenoxy]propanoate;
tert-butyl (2S)-2-[4-bromo-2-(5-methyl-4-butoxy-4,5-dihydroisoxazol-3-yl)phenoxy]propanoate;
tert-butyl (2S)-2-[4-bromo-2-(5-cyclopropyl-4-butoxy-4,5-dihydroisoxazol-3-yl)phenoxy]propanoate;
methyl (2S)-2-[4-chloro-2-(5-cyclopropyl-4-butoxy-4,5-dihydroisoxazol-3-yl)phenoxy]propanoate;
methyl (2S)-2-[4-bromo-2-(5-methyl-4-butoxy-4,5-dihydroisoxazol-3-yl)phenoxy]propanoate;
methyl (2S)-2-[4-bromo-2-(5-cyclopropyl-4-butoxy-4,5-dihydroisoxazol-3-yl)phenoxy]propanoate;
ethyl (2S)-2-[4-chloro-2-(5-cyclopropyl-4-butoxy-4,5-dihydroisoxazol-3-yl)phenoxy]propanoate;
ethyl (2S)-2-[4-bromo-2-(5-methyl-4-butoxy-4,5-dihydroisoxazol-3-yl)phenoxy]propanoate;
ethyl (2S)-2-[4-bromo-2-(5-cyclopropyl-4-butoxy-4,5-dihydroisoxazol-3-yl)phenoxy]propanoate;
tert-butyl (2S)-2-[4-chloro-2-(5-cyclopropyl-4-butoxy-4,5-dihydroisoxazol-3-yl)phenoxy]propanoate;
tert-butyl (2S)-2-[4-bromo-2-(5-methyl-4-butoxy-4,5-dihydroisoxazol-3-yl)phenoxy]propanoate;
tert-butyl (2S)-2-[4-bromo-2-(5-cyclopropyl-4-butoxy-4,5-dihydroisoxazol-3-yl)phenoxy]propanoate;
methyl (2S)-2-[4-bromo-5-fluoro-2-(4-butoxy-4,5-dihydroisoxazol-3-yl)phenoxy]-2-cyclopropylacetate;
methyl (2S)-2-[4-bromo-2-(4-butoxy-4,5-dihydroisoxazol-3-yl)phenoxy]-3-cyclobutylpropanoate;
methyl 2-[4-bromo-5-fluoro-2-(4-butoxy-4,5-dihydroisoxazol-3-yl)phenoxy]acetate;
methyl 2-[4-bromo-2-(4-butoxy-4,5-dihydroisoxazol-3-yl)phenoxy]acetate;
methyl (2S)-2-[4,5-dichloro-2-(4-butoxy-4,5-dihydroisoxazol-3-yl)phenoxy]propanoate;
methyl (2S)-2-[4-bromo-5-fluoro-2-(4-butoxy-4,5-dihydroisoxazol-3-yl)phenoxy]propanoate;
methyl (2S)-2-[4-chloro-5-fluoro-2-(4-butoxy-4,5-dihydroisoxazol-3-yl)phenoxy]propanoate;
methyl (2S)-2-[4-chloro-2-(4-butoxy-4,5-dihydroisoxazol-3-yl)phenoxy]-3-cyclopropylpropanoate;
methyl (2S)-2-[4-fluoro-2-(4-butoxy-4,5-dihydroisoxazol-3-yl)phenoxy]propanoate;
methyl (2S)-2-[4-chloro-2-(4-butoxy-4,5-dihydroisoxazol-3-yl)phenoxy]-3-methylbutanoate;
methyl (2S)-2-[4-chloro-2-(4-butoxy-4,5-dihydroisoxazol-3-yl)phenoxy]butanoate;
methyl (2S)-2-[4-chloro-2-(4-butoxy-4,5-dihydroisoxazol-3-yl)phenoxy]propanoate;
methyl (2S)-2-[4-bromo-2-(4-butoxy-4,5-dihydroisoxazol-3-yl)phenoxy]-3-cyclopropylpropanoate;
methyl (2S)-2-[4-bromo-2-(4-butoxy-4,5-dihydroisoxazol-3-yl)phenoxy]butanoate;
methyl (2S)-2-[4-bromo-2-(4-butoxy-4,5-dihydroisoxazol-3-yl)phenoxy]-3-methylbutanoate;
methyl (2S)-2-[4-bromo-2-(4-butoxy-4,5-dihydroisoxazol-3-yl)phenoxy]propanoate;
ethyl (2S)-2-[4-bromo-5-fluoro-2-(4-butoxy-4,5-dihydroisoxazol-3-yl)phenoxy]-2-cyclopropylacetate;
ethyl (2S)-2-[4-bromo-2-(4-butoxy-4,5-dihydroisoxazol-3-yl)phenoxy]-3-cyclobutylpropanoate;
ethyl 2-[4-bromo-5-fluoro-2-(4-butoxy-4,5-dihydroisoxazol-3-yl)phenoxy]acetate;
ethyl 2-[4-bromo-2-(4-butoxy-4,5-dihydroisoxazol-3-yl)phenoxy]acetate;
ethyl (2S)-2-[4,5-dichloro-2-(4-butoxy-4,5-dihydroisoxazol-3-yl)phenoxy]propanoate;
ethyl (2S)-2-[4-bromo-5-fluoro-2-(4-butoxy-4,5-dihydroisoxazol-3-yl)phenoxy]propanoate;
ethyl (2S)-2-[4-chloro-5-fluoro-2-(4-butoxy-4,5-dihydroisoxazol-3-yl)phenoxy]propanoate;
ethyl (2S)-2-[4-chloro-2-(4-butoxy-4,5-dihydroisoxazol-3-yl)phenoxy]-3-cyclopropylpropanoate;
ethyl (2S)-2-[4-fluoro-2-(4-butoxy-4,5-dihydroisoxazol-3-yl)phenoxy]propanoate;
ethyl (2S)-2-[4-chloro-2-(4-butoxy-4,5-dihydroisoxazol-3-yl)phenoxy]-3-methylbutanoate;
ethyl (2S)-2-[4-chloro-2-(4-butoxy-4,5-dihydroisoxazol-3-yl)phenoxy]butanoate;
ethyl (2S)-2-[4-chloro-2-(4-butoxy-4,5-dihydroisoxazol-3-yl)phenoxy]propanoate;
ethyl (2S)-2-[4-bromo-2-(4-butoxy-4,5-dihydroisoxazol-3-yl)phenoxy]-3-cyclopropylpropanoate;
ethyl (2S)-2-[4-bromo-2-(4-butoxy-4,5-dihydroisoxazol-3-yl)phenoxy]butanoate;

ethyl (2S)-2-[4-bromo-2-(4-butoxy-4,5-dihydroisoxazol-3-yl)phenoxy]-3-methylbutanoate;
ethyl (2S)-2-[4-bromo-2-(4-butoxy-4,5-dihydroisoxazol-3-yl)phenoxy]propanoate;
tert-butyl (2S)-2-[4-bromo-5-fluoro-2-(4-butoxy-4,5-dihydroisoxazol-3-yl)phenoxy]-2-cyclopropylacetate;
tert-butyl (2S)-2-[4-bromo-2-(4-butoxy-4,5-dihydroisoxazol-3-yl)phenoxy]-3-cyclobutylpropanoate;
tert-butyl 2-[4-bromo-5-fluoro-2-(4-butoxy-4,5-dihydroisoxazol-3-yl)phenoxy]acetate;
tert-butyl 2-[4-bromo-2-(4-butoxy-4,5-dihydroisoxazol-3-yl)phenoxy]acetate;
tert-butyl (2S)-2-[4,5-dichloro-2-(4-butoxy-4,5-dihydroisoxazol-3-yl)phenoxy]propanoate;
tert-butyl (2S)-2-[4-bromo-5-fluoro-2-(4-butoxy-4,5-dihydroisoxazol-3-yl)phenoxy]propanoate;
tert-butyl (2S)-2-[4-chloro-5-fluoro-2-(4-butoxy-4,5-dihydroisoxazol-3-yl)phenoxy]propanoate;
tert-butyl (2S)-2-[4-chloro-2-(4-butoxy-4,5-dihydroisoxazol-3-yl)phenoxy]-3-cyclopropylpropanoate;
tert-butyl (2S)-2-[4-fluoro-2-(4-butoxy-4,5-dihydroisoxazol-3-yl)phenoxy]propanoate;
tert-butyl (2S)-2-[4-chloro-2-(4-butoxy-4,5-dihydroisoxazol-3-yl)phenoxy]-3-methylbutanoate;
tert-butyl (2S)-2-[4-chloro-2-(4-butoxy-4,5-dihydroisoxazol-3-yl)phenoxy]butanoate;
tert-butyl (2S)-2-[4-chloro-2-(4-butoxy-4,5-dihydroisoxazol-3-yl)phenoxy]propanoate;
tert-butyl (2S)-2-[4-bromo-2-(4-butoxy-4,5-dihydroisoxazol-3-yl)phenoxy]-3-cyclopropylpropanoate;
tert-butyl (2S)-2-[4-bromo-2-(4-butoxy-4,5-dihydroisoxazol-3-yl)phenoxy]butanoate;
tert-butyl (2S)-2-[4-bromo-2-(4-butoxy-4,5-dihydroisoxazol-3-yl)phenoxy]-3-methylbutanoate;
tert-butyl (2S)-2-[4-bromo-2-(4-butoxy-4,5-dihydroisoxazol-3-yl)phenoxy]propanoate;
methyl (2S)-2-[4-bromo-5-fluoro-2-(4-ethoxy-4,5-dihydroisoxazol-3-yl)phenoxy]-2-cyclopropylacetate;
methyl (2S)-2-[4-bromo-2-(4-ethoxy-4,5-dihydroisoxazol-3-yl)phenoxy]-3-cyclobutylpropanoate;
methyl 2-[4-bromo-5-fluoro-2-(4-ethoxy-4,5-dihydroisoxazol-3-yl)phenoxy]acetate;
methyl 2-[4-bromo-2-(4-ethoxy-4,5-dihydroisoxazol-3-yl)phenoxy]acetate;
methyl (2S)-2-[4,5-dichloro-2-(4-ethoxy-4,5-dihydroisoxazol-3-yl)phenoxy]propanoate;
methyl (2S)-2-[4-bromo-5-fluoro-2-(4-ethoxy-4,5-dihydroisoxazol-3-yl)phenoxy]propanoate;
methyl (2S)-2-[4-chloro-5-fluoro-2-(4-ethoxy-4,5-dihydroisoxazol-3-yl)phenoxy]propanoate;
methyl (2S)-2-[4-chloro-2-(4-ethoxy-4,5-dihydroisoxazol-3-yl)phenoxy]-3-cyclopropylpropanoate;
methyl (2S)-2-[4-fluoro-2-(4-ethoxy-4,5-dihydroisoxazol-3-yl)phenoxy]propanoate;
methyl (2S)-2-[4-chloro-2-(4-ethoxy-4,5-dihydroisoxazol-3-yl)phenoxy]-3-methylbutanoate;
methyl (2S)-2-[4-chloro-2-(4-ethoxy-4,5-dihydroisoxazol-3-yl)phenoxy]butanoate;
methyl (2S)-2-[4-chloro-2-(4-ethoxy-4,5-dihydroisoxazol-3-yl)phenoxy]propanoate;
methyl (2S)-2-[4-bromo-2-(4-ethoxy-4,5-dihydroisoxazol-3-yl)phenoxy]-3-cyclopropylpropanoate;
methyl (2S)-2-[4-bromo-2-(4-ethoxy-4,5-dihydroisoxazol-3-yl)phenoxy]butanoate;
methyl (2S)-2-[4-bromo-2-(4-ethoxy-4,5-dihydroisoxazol-3-yl)phenoxy]-3-methylbutanoate;
methyl (2S)-2-[4-bromo-2-(4-ethoxy-4,5-dihydroisoxazol-3-yl)phenoxy]propanoate;
ethyl (2S)-2-[4-bromo-5-fluoro-2-(4-ethoxy-4,5-dihydroisoxazol-3-yl)phenoxy]-2-cyclopropylacetate;
ethyl (2S)-2-[4-bromo-2-(4-ethoxy-4,5-dihydroisoxazol-3-yl)phenoxy]-3-cyclobutylpropanoate;
ethyl 2-[4-bromo-5-fluoro-2-(4-ethoxy-4,5-dihydroisoxazol-3-yl)phenoxy]acetate;
ethyl 2-[4-bromo-2-(4-ethoxy-4,5-dihydroisoxazol-3-yl)phenoxy]acetate;
ethyl (2S)-2-[4,5-dichloro-2-(4-ethoxy-4,5-dihydroisoxazol-3-yl)phenoxy]propanoate;
ethyl (2S)-2-[4-bromo-5-fluoro-2-(4-ethoxy-4,5-dihydroisoxazol-3-yl)phenoxy]propanoate;
ethyl (2S)-2-[4-chloro-5-fluoro-2-(4-ethoxy-4,5-dihydroisoxazol-3-yl)phenoxy]propanoate;
ethyl (2S)-2-[4-chloro-2-(4-ethoxy-4,5-dihydroisoxazol-3-yl)phenoxy]-3-cyclopropylpropanoate;
ethyl (2S)-2-[4-fluoro-2-(4-ethoxy-4,5-dihydroisoxazol-3-yl)phenoxy]propanoate;
ethyl (2S)-2-[4-chloro-2-(4-ethoxy-4,5-dihydroisoxazol-3-yl)phenoxy]-3-methylbutanoate;
ethyl (2S)-2-[4-chloro-2-(4-ethoxy-4,5-dihydroisoxazol-3-yl)phenoxy]butanoate;
ethyl (2S)-2-[4-chloro-2-(4-ethoxy-4,5-dihydroisoxazol-3-yl)phenoxy]propanoate;
ethyl (2S)-2-[4-bromo-2-(4-ethoxy-4,5-dihydroisoxazol-3-yl)phenoxy]-3-cyclopropylpropanoate;
ethyl (2S)-2-[4-bromo-2-(4-ethoxy-4,5-dihydroisoxazol-3-yl)phenoxy]butanoate;
ethyl (2S)-2-[4-bromo-2-(4-ethoxy-4,5-dihydroisoxazol-3-yl)phenoxy]-3-methylbutanoate;
ethyl (2S)-2-[4-bromo-2-(4-ethoxy-4,5-dihydroisoxazol-3-yl)phenoxy]propanoate;
tert-butyl (2S)-2-[4-bromo-5-fluoro-2-(4-ethoxy-4,5-dihydroisoxazol-3-yl)phenoxy]-2-cyclopropylacetate;
tert-butyl (2S)-2-[4-bromo-2-(4-ethoxy-4,5-dihydroisoxazol-3-yl)phenoxy]-3-cyclobutylpropanoate;
tert-butyl 2-[4-bromo-5-fluoro-2-(4-ethoxy-4,5-dihydroisoxazol-3-yl)phenoxy]acetate;
tert-butyl 2-[4-bromo-2-(4-ethoxy-4,5-dihydroisoxazol-3-yl)phenoxy]acetate;
tert-butyl (2S)-2-[4,5-dichloro-2-(4-ethoxy-4,5-dihydroisoxazol-3-yl)phenoxy]propanoate;
tert-butyl (2S)-2-[4-bromo-5-fluoro-2-(4-ethoxy-4,5-dihydroisoxazol-3-yl)phenoxy]propanoate;
tert-butyl (2S)-2-[4-chloro-5-fluoro-2-(4-ethoxy-4,5-dihydroisoxazol-3-yl)phenoxy]propanoate;
tert-butyl (2S)-2-[4-chloro-2-(4-ethoxy-4,5-dihydroisoxazol-3-yl)phenoxy]-3-cyclopropylpropanoate;
tert-butyl (2S)-2-[4-fluoro-2-(4-ethoxy-4,5-dihydroisoxazol-3-yl)phenoxy]propanoate;
tert-butyl (2S)-2-[4-chloro-2-(4-ethoxy-4,5-dihydroisoxazol-3-yl)phenoxy]-3-methylbutanoate;
tert-butyl (2S)-2-[4-chloro-2-(4-ethoxy-4,5-dihydroisoxazol-3-yl)phenoxy]butanoate;
tert-butyl (2S)-2-[4-chloro-2-(4-ethoxy-4,5-dihydroisoxazol-3-yl)phenoxy]propanoate;
tert-butyl (2S)-2-[4-bromo-2-(4-ethoxy-4,5-dihydroisoxazol-3-yl)phenoxy]-3-cyclopropylpropanoate;
tert-butyl (2S)-2-[4-bromo-2-(4-ethoxy-4,5-dihydroisoxazol-3-yl)phenoxy]butanoate;
tert-butyl (2S)-2-[4-bromo-2-(4-ethoxy-4,5-dihydroisoxazol-3-yl)phenoxy]-3-methylbutanoate; and
tert-butyl (2S)-2-[4-bromo-2-(4-ethoxy-4,5-dihydroisoxazol-3-yl)phenoxy]propanoate.

This disclosure is also directed, in part, to pharmaceutical compositions comprising compounds of Formula I prepared by the disclosed processes. In one embodiment, a compound of Formula I prepared by the above process may be included in pharmaceutical compositions. These compositions may also comprise one or more conventional pharmaceutically acceptable carriers. The compositions may comprise further active ingredients/agents or other components to increase the efficiency of the composition.

Thus, another aspect of the disclosure is a process for preparing a pharmaceutical composition comprising a compound of Formula I, characterized in that the compound of Formula I is prepared by a process according to the present invention.

A pharmaceutical composition comprising a compound of Formula I of the disclosure and a pharmaceutically acceptable carrier constitutes another aspect of the invention.

Items

1. A process for the preparation of compounds of Formula I

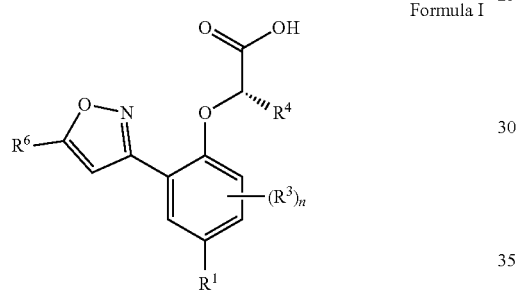

Formula I comprising step a) wherein
i) a compound of Formula II is reacted with an acid or base Formula II and
ii) a compound of Formula I is isolated from the reaction mixture,
wherein
R$^1$ is selected from the group consisting of H, F, Cl, Br and I;
R$^2$ is selected from the group consisting of C$_{1-5}$ alkyl and C$_{3-5}$ cycloalkyl
R$^3$ is selected from the group consisting of deuterium, F, Cl, Br and I;
R$^4$ is selected from the group consisting of H, deuterium, C$_{1-5}$ alkyl, C$_{2-5}$ alkenyl, C$_{2-5}$ alkynyl, C$_{3-5}$ cycloalkyl and C$_5$ cycloalkenyl, each of which may be optionally substituted with one or more, identical or different, substituents R$^7$;
R$^5$ is selected from the group consisting of C$_{1-5}$ alkyl optionally substituted with one or more, identical or different, substituents R$^8$, C$_{2-5}$ alkenyl, C$_{2-5}$ alkynyl, C$_{3-6}$ cycloalkyl optionally substituted with one or more, identical or different, substituents R$^8$, phenyl optionally substituted with one or more, identical or different, substituents R$^9$ and benzyl optionally substituted with one or more, identical or different, substituents R$^9$;
R$^6$ is selected from the group consisting of H, deuterium C$_{1-5}$ alkyl and C$_{3-5}$ cycloalkyl;
R$^7$ is independently selected from the group consisting of deuterium, tritium, F, Cl, Br, I, CN, isocyanide, R$^7$ is C$_{3-5}$ cycloalkyl optionally substituted with one or more, identical or different, substituents R$^8$, O—C$_{1-3}$ alkyl optionally substituted with one or more, identical or different, substituents R$^8$, S—C$_{1-3}$ alkyl optionally substituted with one or more, identical or different, substituents R$^8$, CH$_2$—O—C$_{1-3}$ alkyl optionally substituted with one or more, identical or different, substituents R$^8$ and CH$_2$—S—C$_{1-3}$ alkyl optionally substituted with one or more, identical or different, substituents R$^8$;
R$^8$ is independently selected from the group consisting of deuterium and F;
R$^9$ is independently selected from the group consisting of deuterium, methoxy, nitro, cyano, Cl, Br, I and F; and
n is an integer 0, 1, 2 or 3.
2. The process of any of the previous items, wherein R$^1$ is Cl or Br.
3. The process of any of the previous items, wherein R$^1$ is Cl.
4. The process of any of the previous items, wherein R$^1$ is Br.
5. The process of any of the previous items, wherein R$^2$ is C$_{1-5}$ alkyl.
6. The process of any of the previous items, wherein R$^2$ is selected from the group consisting of methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.
7. The process of any of the previous items, wherein R$^2$ is ethyl.
8. The process of any of the previous items, wherein R$^2$ is prop-1-yl.
9. The process of any of the previous items, wherein R$^2$ is prop-2-yl.
10. The process of any of the previous items, wherein R$^2$ is but-1-yl.
11. The process of any of the previous items, wherein R$^2$ is 2-methyl-prop-2-yl.
12. The process of any of the previous items, wherein R$^3$ is F.
13. The process of any of the previous items, wherein R$^3$ is deuterium.
14. The process of any of the previous items, wherein R$^4$ is H.
15. The process of any of the previous items, wherein R$^4$ is C$_{1-5}$ alkyl optionally substituted with one or more, identical or different, substituents R$^7$.

16. The process of any of the previous items, wherein $R^4$ is Me.
17. The process of any of the previous items, wherein $R^4$ is Et.
18. The process of any of the previous items, wherein $R^4$ is —$CH_2F$.
19. The process of any of the previous items, wherein $R^4$ is cyclopropyl.
20. The process of any of the previous items, wherein $R^5$ is $C_{1-5}$ alkyl optionally substituted with one or more, identical or different, substituents $R^3$.
21. The process of any of the previous items, wherein $R^5$ is Me.
22. The process of any of the previous items, wherein $R^5$ is Et.
23. The process of any of the previous items, wherein $R^5$ is 2-methyl-prop-2-yl.
24. The process of any of the previous items, wherein $R^6$ is H.
25. The process of any of the previous items, wherein $R^6$ is D.
26. The process of any of the previous items, wherein $R^6$ is $C_{1-5}$ alkyl.
27. The process of any of the previous items, wherein $R^6$ is selected from the group consisting of methyl, ethyl, prop-1-yl, prop-2-yl, 2-methyl-prop-1-yl, 2-methyl-prop-2-yl, 2,2-dimethyl-prop-1-yl, but-1-yl, but-2-yl, 3-methyl-but-1-yl, 3-methyl-but-2-yl, pent-1-yl, pent-2-yl and pent-3-yl.
28. The process of any of the previous items, wherein $R^7$ is deuterium.
29. The process of any of the previous items, wherein $R^7$ is F.
30. The process of any of the previous items, wherein $R^7$ is $C_{3-5}$ cycloalkyl optionally substituted with one or more, identical or different, substituents $R^8$.
31. The process of any of the previous items, wherein $R^4$ is $C_{1-5}$ alkyl substituted with $R^7$, wherein $R^7$ is $C_{3-5}$ cycloalkyl optionally substituted with one or more, identical or different, substituents $R^8$.
32. The process of any of the previous items, wherein n=0.
33. The process of any of the previous items, wherein n=1.
34. The process of any of the previous items, wherein n=2.
35. The process of any of the previous items, wherein n=3.
36. The process of any of the previous items, wherein the compound of Formula II is reacted with a base.
37. The process of any of the previous items, wherein the compound of Formula II is reacted with an acid.
38. The process of any of the previous items, wherein the compound of Formula II is reacted with a concentrated acid.
39. The process of any of the previous items, wherein the compound of Formula II is reacted with an acid selected from the group formic acid, acetic acid, propionic acid, butyric acid, benzoic acid, hydrochloric acid and sulfuric acid or a mixture thereof.
40. The process of any of the previous items, wherein the compound of Formula II is reacted with concentrated formic acid.
41. The process of any of the previous items, wherein the compound of Formula II is reacted with concentrated acetic acid.
42. The process of any of the previous items, wherein the compound of Formula II is reacted with a mixture of concentrated formic acid and concentrated acetic acid.
43. The process of any of the previous items, wherein step a) is performed at a temperature of between 70° C. and 140° C., such as between 80° C. and 130° C., such as between 90° C. and 120° C.
44. The process of any of the previous items, wherein the reaction time of step a) is between 12 hours and 96 hours, such as between 24 and 72 hours, such as between 36 and 60 hours.
45. The process of any of the previous items, wherein the amount of acid used in step a) i) is between 3 mL per gram of starting material and 15 mL per gram of starting material.
46. The process of any of the previous items, wherein the compound of Formula I is isolated from the reaction mixture in step b) by adding water and extracting the product into an organic solvent.
47. The process of any of the previous items, wherein the compound of Formula I is isolated from the reaction mixture in step b) by adding water and extracting the product into an organic solvent selected from the list consisting of toluene, ethyl acetate, isopropyl acetate and tert-butyl methyl ether.
48. The process of any of the previous items, wherein the compound of Formula I is purified by crystallisation from an organic solvent.
49. The process of any of the previous items, wherein the compound of Formula I is purified by crystallisation from an organic solvent selected from the list consisting of toluene, ethyl acetate, isopropyl acetate and tert-butyl methyl ether.
50. The process of any of the previous items, wherein the process further comprises step b) wherein
i) a compound of Formula III

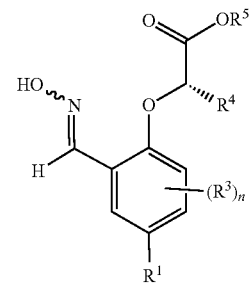

Formula III is reacted with N-chlorosuccinimide in an organic solvent;
ii) a compound of Formula IV

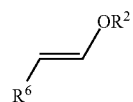

Formula IV and a base are added to the reaction mixture; and
iii) a compound of Formula II is isolated from the reaction mixture,
wherein $R^1$ to $R^9$ and n are defined as in item 1.

51. The process of any of the previous items, wherein the solvent in step b) i) is dimethylformamide (DMF).
52. The process of any of the previous items, wherein the compound of formula IV is selected from the group consisting of ethyl vinyl ether, n-butyl vinyl ether and tert-butyl vinyl ether.
53. The process of any of the previous items, wherein the base in step b) ii) is selected from the group consisting of trimethylamine, triethylamine, triisopropylamine and N,N-diisopropylethylamine.
54. The process of any of the previous items, wherein the process further comprises step c) wherein
i) a compound of Formula V

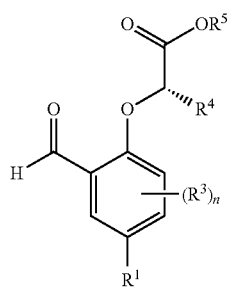

Formula V is reacted with hydroxylamine in an organic solvent;
ii) a base is added to the reaction mixture; and
iii) a compound of Formula III is isolated from the reaction mixture,
wherein $R^1$ to $R^9$ and n are defined as in claim 1.
55. The process of any of the previous items, wherein the organic solvent in step c) i) is an alcohol.
56. The process of any of the previous items, wherein the organic solvent in step c) i) is an alcohol selected from the group consisting of methanol, ethanol, propanol, n-butanol and tert-butanol.
57. The process of any of the previous items, wherein the base in step c) ii) is selected from the group consisting of pyridine, trimethylamine, triethylamine, triisopropylamine and N,N-diisopropylethylamine.
58. The process of any of the previous items, wherein the process further comprises step d) wherein
i) a compound of Formula VI

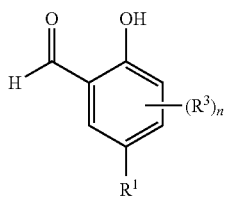

Formula VI is added to a compound of Formula VII in an organic solvent;

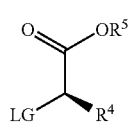

Formula VI ii) a base is added to the reaction mixture; and
iii) a compound of Formula V is isolated from the reaction mixture,
wherein $R^1$ to $R^9$ and n are as defined herein and LG is a leaving group.
59. The process of any of the previous items, wherein the leaving group (LG) of Formula VI is selected from the group consisting of tosylate, mesylate, triflate, nosylate, brosylate, bromide, iodide and chloride.
60. The process of any of the previous items, wherein the leaving group (LG) of Formula VI is tosylate.
61. The process of any of the previous items, wherein the organic solvent is selected from the group consisting of pentane, hexane, heptane, toluene, xylene, dichloromethane, tetrahydrofuran and acetonitrile.
62. The process of any of the previous items, wherein the base in step d) ii) is an inorganic base.
63. The process of any of the previous items, wherein the base in step d) ii) is an inorganic base selected from the group consisting of lithium carbonate, sodium carbonate, potassium carbonate, caesium carbonate, lithium hydrogencarbonate, sodium hydrogencarbonate, potassium hydrogencarbonate, lithium hydroxide, sodium hydroxide and potassium hydroxide.
64. The process of any of the previous items, wherein the compound of Formula I is selected from the group consisting of:
(2S)-2-[4-bromo-5-fluoro-2-(1,2-oxazol-3-yl)phenoxy]-2-cyclopropylacetic acid;
(2S)-2-[4-bromo-2-(1,2-oxazol-3-yl)phenoxy]-3-cyclobutylpropanoic acid;
2-[4-bromo-5-fluoro-2-(1,2-oxazol-3-yl)phenoxy]acetic acid;
2-[4-bromo-2-(1,2-oxazol-3-yl)phenoxy]acetic acid;
(2S)-2-[4,5-dichloro-2-(1,2-oxazol-3-yl)phenoxy]propanoic acid;
(2S)-2-[4-bromo-5-fluoro-2-(1,2-oxazol-3-yl)phenoxy]propanoic acid;
(2S)-2-[4-chloro-5-fluoro-2-(1,2-oxazol-3-yl)phenoxy]propanoic acid;
(2S)-2-[4-chloro-2-(1,2-oxazol-3-yl)phenoxy]-3-cyclopropylpropanoic acid;
(2S)-2-[4-fluoro-2-(1,2-oxazol-3-yl)phenoxy]propanoic acid;
(2S)-2-[4-chloro-2-(5-cyclopropyl-1,2-oxazol-3-yl)phenoxy]propanoic acid;
(2S)-2-[4-chloro-2-(1,2-oxazol-3-yl)phenoxy]-3-methylbutanoic acid;
(2S)-2-[4-chloro-2-(1,2-oxazol-3-yl)phenoxy]butanoic acid;
(2S)-2-[4-chloro-2-(1,2-oxazol-3-yl)phenoxy]propanoic acid;
(2S)-2-[4-bromo-2-(1,2-oxazol-3-yl)phenoxy]-3-cyclopropylpropanoic acid;
(2S)-2-[4-bromo-2-(1,2-oxazol-3-yl)phenoxy]butanoic acid;
(2S)-2-[4-bromo-2-(1,2-oxazol-3-yl)phenoxy]-3-methylbutanoic acid;
(2S)-2-[4-bromo-2-(5-methyl-1,2-oxazol-3-yl)phenoxy] propanoic acid;
(2S)-2-[4-bromo-2-(5-cyclopropyl-1,2-oxazol-3-yl)phenoxy]propanoic acid; and
(2 S)-2-[4-bromo-2-(1,2-oxazol-3-yl)phenoxy]propanoic acid.
65. The process of any of the previous items, wherein the compound of Formula I is an inhibitor of the ClC-1 chloride ion channel.
66. The process of any one of the previous items, wherein the compound of Formula I is at least 80% pure, such as at least 90% pure, such as at least 95% pure, such as at least 96% pure, such as at least 97% pure, such as at least 98% pure.

67. A process for the preparation of a pharmaceutical composition comprising the steps of
i) preparing a compound selected from the group consisting of (2 S)-2-[4-bromo-5-fluoro-2-(1,2-oxazol-3-yl)phenoxy]-2-cyclopropylacetic acid;

(2S)-2-[4-bromo-2-(1,2-oxazol-3-yl)phenoxy]-3-cyclobutylpropanoic acid;

2-[4-bromo-5-fluoro-2-(1,2-oxazol-3-yl)phenoxy]acetic acid;

2-[4-bromo-2-(1,2-oxazol-3-yl)phenoxy]acetic acid;

(2S)-2-[4,5-dichloro-2-(1,2-oxazol-3-yl)phenoxy]propanoic acid;

(2S)-2-[4-bromo-5-fluoro-2-(1,2-oxazol-3-yl)phenoxy]propanoic acid;

(2 S)-2-[4-chloro-5-fluoro-2-(1,2-oxazol-3-yl)phenoxy]propanoic acid;

(2S)-2-[4-chloro-2-(1,2-oxazol-3-yl)phenoxy]-3-cyclopropylpropanoic acid;

(2S)-2-[4-fluoro-2-(1,2-oxazol-3-yl)phenoxy]propanoic acid;

(2 S)-2-[4-chloro-2-(5-cyclopropyl-1,2-oxazol-3-yl)phenoxy]propanoic acid;

(2 S)-2-[4-chloro-2-(1,2-oxazol-3-yl)phenoxy]-3-methylbutanoic acid;

(2S)-2-[4-chloro-2-(1,2-oxazol-3-yl)phenoxy]butanoic acid;

(2S)-2-[4-chloro-2-(1,2-oxazol-3-yl)phenoxy]propanoic acid;

(2S)-2-[4-bromo-2-(1,2-oxazol-3-yl)phenoxy]-3-cyclopropylpropanoic acid;

(2S)-2-[4-bromo-2-(1,2-oxazol-3-yl)phenoxy]butanoic acid;

(2S)-2-[4-bromo-2-(1,2-oxazol-3-yl)phenoxy]-3-methylbutanoic acid;

(2S)-2-[4-bromo-2-(5-methyl-1,2-oxazol-3-yl)phenoxy]propanoic acid;

(2 S)-2-[4-bromo-2-(5-cyclopropyl-1,2-oxazol-3-yl)phenoxy]propanoic acid; and (2S)-2-[4-bromo-2-(1,2-oxazol-3-yl)phenoxy]propanoic acid according to any of the previous items; and ii) formulating said compound into a pharmaceutical composition.

EXAMPLES

Materials and Methods

NMR Spectra $^1$H-NMR spectra were recorded either on a Jeol LA400 (400 MHz) spectrometer and were calibrated using residual nondeuterated solvent as internal reference (7.24 ppm for $CHCl_3$).

LCMS Method

Equipment: Agilent 1260 Infinity series LC (High Pressure Degasser, Binary Pump, Autosampler and Column Oven) with Agilent 1100 DAD detector scanning from 210 nm to 315 nm. Mass detection was afforded with API 2000 mass spectrometer (electrospray).

Column: Agilent Poroshell 120 EC-C18 (2.7 m, 3.0×50 mm).

Conditions: 0.1% v/v Formic acid in water [eluent A]; MeCN [eluent B]; Flow rate 0.8 mL/min and 1.5 minutes equilibration time between samples.

Gradient

| Time (min) | Eluent A (%) | Eluent B (%) |
|---|---|---|
| 0.01 | 95 | 5 |
| 0.20 | 95 | 5 |
| 2.00 | 5 | 95 |
| 3.00 | 5 | 95 |
| 3.25 | 95 | 5 |
| 3.50 | 95 | 5 |

Chiral SCF Method

Compounds were analysed using a Waters ACQUITY ultra-performance convergence chromatography (UPC2) system equipped with a binary solvent delivery pump, an auto-sampler, a column oven (CM-30S), a back-pressure regulator, and a diode array detector.

Column: Lux A1 (4.6 mm×250 mm, 5 m).

Conditions: 40° C., 4 mL/min, isocratic 15:85 EtOH:CO$_2$ (0.1% v/v TFA), 125 BarG.

Example 1: Synthesis of (2S)-2-(4-bromo-2-(isoxazol-3-yl)phenoxy)propanoic acid (S)-2-(4-Bromo-2-(isoxazol-3-yl)phenoxy)propanoic acid B.6 was prepared using the schematic shown below.

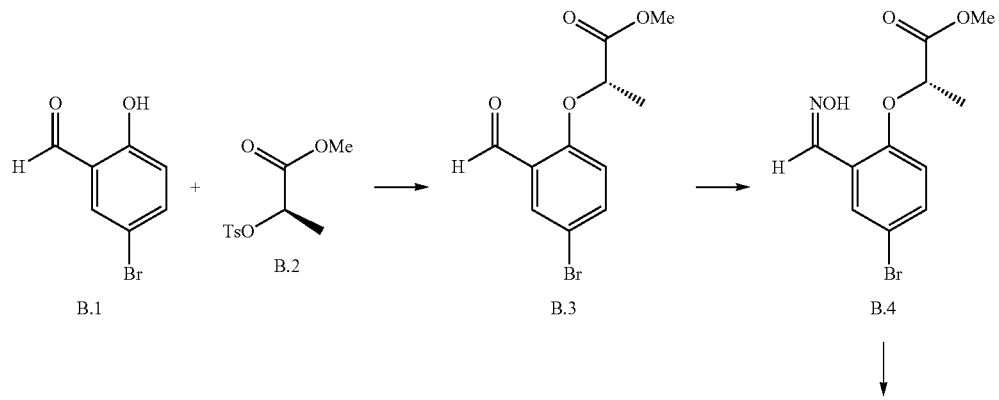

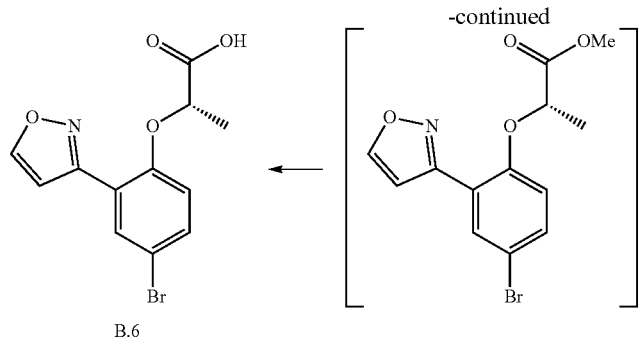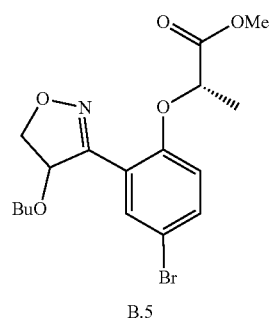

Synthesis of methyl (S)-2-(4-bromo-2-formylphenoxy)propanoate B.3

5-Bromo-2-hydroxybenzaldehyde B.1 (9.26 g, 46.10 mmol) was added to a stirred solution of methyl (R)-2-(tosyloxy)propanoate B.2 (11.90 g, 46.10 mmol) in hexane (180 mL) and the resulting mixture was heated to 80° C. until dissolution. Potassium carbonate (12.74 g, 92.20 mmol) was added to the reaction mixture and it was stirred at 80° C. for 36 h and at room temperature for 60 h.

Solvent was removed in vacuo and the residue was partitioned between water (400 mL) and ethyl acetate (400 mL). The aqueous layer was extracted with more ethyl acetate. The organic layers were combined together and were washed with water (2×300 mL) and brine, dried over sodium sulfate, filtered and concentrated under reduced pressure in order to afford a pale yellow oil. This crude material was purified via silica gel flash column chromatography using heptane:ethyl acetate 10-20% as solvent system in order to afford the desired product, methyl (S)-2-(4-bromo-2-formylphenoxy)propanoate B.3, as a colourless oil, which solidified overnight (8.08 g, 62% yield).

1H NMR (400 MHz, CDCl$_3$) δ 10.54 (s, 1H), 7.94 (d, J=2.7 Hz, 1H), 7.56 (dd, J=8.9, 2.7 Hz, 1H), 6.71 (d, J=8.9 Hz, 1H), 4.84 (q, J=6.8 Hz, 1H), 3.74 (s, 3H), 1.68 (d, J=6.8 Hz, 3H). LC/MS (Agilent) m/z 286.8 (M+H)$^+$ at 2.54 mins.

Synthesis of methyl (S,E)-2-(4-bromo-2-((hydroxyimino)-methyl)phenoxy)propanoate B.4

Hydroxyamine hydrochloride (1.87 g, 26.90 mmol) was added under nitrogen to a stirred solution of methyl (S)-2-(4-bromo-2-formylphenoxy)propanoate B.3 (7.25 g, 26.90 mmol) in methanol (150 mL), previously cooled to −40° C. Then, pyridine (2.6 mL, 29.60 mmol) was added dropwise to the mixture and it was stirred at that temperature for 1 h. The reaction mixture was stored at 4° C. overnight.

The reaction mixture was warmed to room temperature and was poured into water (400 mL). This solution was extracted with ethyl acetate (2×400 mL). The organic layers were combined together and were washed with water (2×300 mL) and brine, dried over sodium sulfate, filtered and concentrated under reduced pressure in order to afford the desired product, methyl (S,E)-2-(4-bromo-2-((hydroxyimino)-methyl)phenoxy)propanoate B.4, as a white solid (8.20 g, quantitative yield).

1H NMR (400 MHz, CDCl$_3$) δ 8.49 (s, 1H), 7.87 (d, J=2.6 Hz, 1H), 7.35 (dd, J=8.8, 2.6 Hz, 1H), 6.61 (d, J=8.8 Hz, 1H), 4.74 (q, J=6.8 Hz, 1H), 3.72 (s, 3H), 1.63 (d, J=6.8 Hz, 3H). LC/MS (Agilent) m/z 301.9 (M+H)$^+$ at 2.42 mins.

Synthesis of methyl (2S)-2-(4-bromo-2-(4-butoxy-4,5-dihydroisoxazol-3-yl)phenoxy)propanoate B.5

N-Chlorosuccinimide (3.90 g, 28.95 mmol) was added to a solution of methyl (S,E)-2-(4-bromo-2-((hydroxyimino) methyl)phenoxy)propanoate B.4 (7.95 g, 26.40 mmol) in dimethylformamide (200 mL) at room temperature, followed by the addition of a 1M solution of hydrochloric acid (1 mL aqueous). The resulting reaction mixture was stirred at room temperature for 75 min. After that time, the mixture was cooled to 0° C. and triethylamine (4.42 mL, 31.70 mmol) was added to it, followed by the addition of butyl vinyl ether (4.1 mL, 31.70 mmol). The reaction mixture was stirred at room temperature for 3.5 h.

The reaction mixture was poured into water (350 mL), acidified with a 1M solution of hydrochloric acid to pH 5 and it was extracted with tert-butylmethyl ether (2×350 mL). The organic layers were combined together and they were washed with water and brine, dried over sodium sulfate, filtered and concentrated under reduced pressure in order to afford the desired product, methyl (2S)-2-(4-bromo-2-(4-butoxy-4,5-dihydroisoxazol-3-yl)phenoxy)propanoate B.5 (a ca. 1:1 mixture of diastereoisomers), as a yellow oil (10.30 g, 98% yield).

1H NMR (400 MHz, CDCl$_3$) δ 7.99 and 7.97 (two d, J=2.5 Hz, 1H), 7.37 (dd, J=8.9, 2.5 Hz, 1H), 6.63 and 6.61 (two d, J=8.9 Hz, 1H), 5.62 (m, 1H), 4.78 (m, 1H), 3.81 (m, 1H), 3.73 and 3.71 (two s, 3H), 3.59 (m, 1H), 3.48 (m, 1H), 3.35 and 3.31 (two dd, J=13.4, 1.5 Hz, 1H), 1.61 (d, J=6.8 Hz, 3H), 1.56 (m, 2H), 1.35 (m, 2H), 0.90 and 0.89 (two t, J=7.4 Hz, 3H). LC/MS (Agilent) m/z 399.9 (M+H)$^+$ at 2.91 mins.

Synthesis of (2S)-2-(4-bromo-2-(isoxazol-3-yl)phenoxy)propanoic acid B.6

A solution of ethyl (2S)-2-(4-bromo-2-(4-butoxy-4,5-dihydroisoxazol-3-yl)phenoxy)propanoate B.5 (9.15 g, 22.90 mmol) in aqueous formic acid (90%) (100 mL, 2.39 mol) was heated at 100° C. for 6 h.

The reaction mixture was cooled to room temperature and solvent was removed in vacuo. The crude material was azeotroped with acetonitrile and dried in vacuo for 1 h at 40° C. The isolated oil was partitioned between tert-butylmethyl ether and water. The organic layer was dried over sodium sulfate, filtered and concentrated under reduced pressure in order to give a yellow oil. This oil was triturated in dichloromethane (20 mL) and hexane (400 mL) and the isolated solid was dried overnight in the vacuum oven in order to afford the desired product, (2S)-2-(4-bromo-2-(isoxazol-3-yl)phenoxy)propanoic acid B.6, as a beige solid (5.52 g, 78% yield).

1H NMR (400 MHz, CDCl$_3$) δ 8.49 (d, J=1.8 Hz, 1H), 7.77 (d, J=2.4 Hz, 1H), 7.53 (dd, J=8.8, 2.4 Hz, 1H), 6.90 (d, J=8.8 Hz, 1H), 6.78 (d, J=1.8 Hz, 1H), 4.91 (q, J=6.9 Hz, 1H), 1.73 (d, J=6.9 Hz, 3H). LC/MS (Agilent) m/z 312.0 (M+H)$^+$ at 2.40 mins.

The overall yield was 48% starting from 5-bromo-2-hydroxybenzaldehyde B.1 and the product was >98% pure as judged by LC/MS and 1H NMR.

Chiral SCF method: (S)-enantiomer 2.12 mins; (R)-enantiomer 2.79 mins.

Example 2: Synthesis of (2S)-2-(4-bromo-2-(isoxazol-3-yl)phenoxy)propanoic acid

Synthesis of methyl (2S)-2-(4-bromo-2-(4-butoxy-4,5-dihydroisoxazol-3-yl)phenoxy)propanoate B.5

DMF (595 mL) was added to methyl (S,E)-2-(4-bromo-2-((hydroxyimino)methyl)phenoxy)propanoate B.4 (119 g) and the temperature adjusted to 20° C. N-chlorosuccinimide (16.0 g, 0.3 eq) was added and the reaction was stirred for 20 minutes at 15-30° C. N-chlorosuccinimide (4×10.5 g, 4×0.2 eq) was added in 4 equal portions every 5 minutes keeping the temperature between 20-30° C. and the reaction was stirred for 20 minutes at 15-30° C. The reaction was cooled to 0-5° C. and butyl vinyl ether (56.6 mL, 1.1 eq) was added followed by triethylamine (54.9 mL, 1.0 eq) dropwise at 0-5° C. over 1 hour. The reaction was stirred at 0-5° C. over 12 hours then water (1.19 L) was added over 5 minutes. The product was extracted with tert-butyl methyl ether (2×600 mL) and the organic phase washed with 10% w/w brine (2×350 mL), dried over magnesium sulfate, filtered and concentrated to give methyl (2S)-2-(4-bromo-2-(4-butoxy-4,5-dihydroisoxazol-3-yl)phenoxy)propanoate B.5 as a ca. 1:1 mixture of diastereoisomers (157.1 g, quantitative) as an amber oil.

Synthesis of (2S)-2-(4-bromo-2-(isoxazol-3-yl)phenoxy)propanoic acid B.6

(2S)-2-(4-bromo-2-(4-butoxy-4,5-dihydroisoxazol-3-yl) phenoxy)propanoate B.5 (151 g) was dissolved in acetic acid (755 mL) and water (226 mL) was added at 15-25° C. The reaction was heated to reflux (ca. 107° C.) for 48 hours or until in process control showed that the reaction was complete. The reaction was cooled to 15-25° C. and water (1.5 L) was added. The product was extracted with tert-butyl methyl ether (755 mL then 450 mL) and the combined organic phases washed with 10% w/w brine (3×450 mL). The organic phase was distilled leaving ca. 4 volumes then toluene (1.5 L) was added. The organic phase was distilled leaving ca. 5 volumes then toluene (750 mL) was added. The organic phase was distilled leaving ca. 4 volumes then cooled to 80-90° C. and filtered. The organic phase was cooled to 50-55° C., a seed crystal was added. The solution was stirred at 50-55° C. for 30 minutes, cooled to 0-5° C. over 12 hours, stirred at 0-5° C. for 5 hours, then filtered washing toluene (150 mL) and n-heptane (2×300 mL). The solid was dried at 40° C. until no further change in mass giving (2S)-2-(4-bromo-2-(isoxazol-3-yl)phenoxy)propanoic acid B.6 as a beige solid (83.9 g, 71%) in >98% purity as determined by LC/MS and 1H NMR and >98% enantiomeric excess as determined by chiral HPLC.

Example 3: Screening of Compounds on the Human Isoform of ClC-1 Expressed in CHO Cells Using Automated Patch-Clamp The investigatory goal of these experiments was to evaluate how compounds affect the open probability and current amplitude of human ClC-1 channels expressed in CHO cells. Experiments were performed using an automated patch clamp system that allowed high throughput testing of whole cell patches together with both intracellular and extracellular addition of compound.

Automated Voltage Clamp Measurements

Automated whole cell patch clamp experiments were performed with the Qpatch 16 system (Sophion Bioscience, Ballerup, Denmark) at room temperature. Data acquisition and analysis were performed in the Qassay software (ver. 5.6, Odense).

Voltage Protocol and Analysis of Whole Cell ClC-1 Currents

Figure 2:
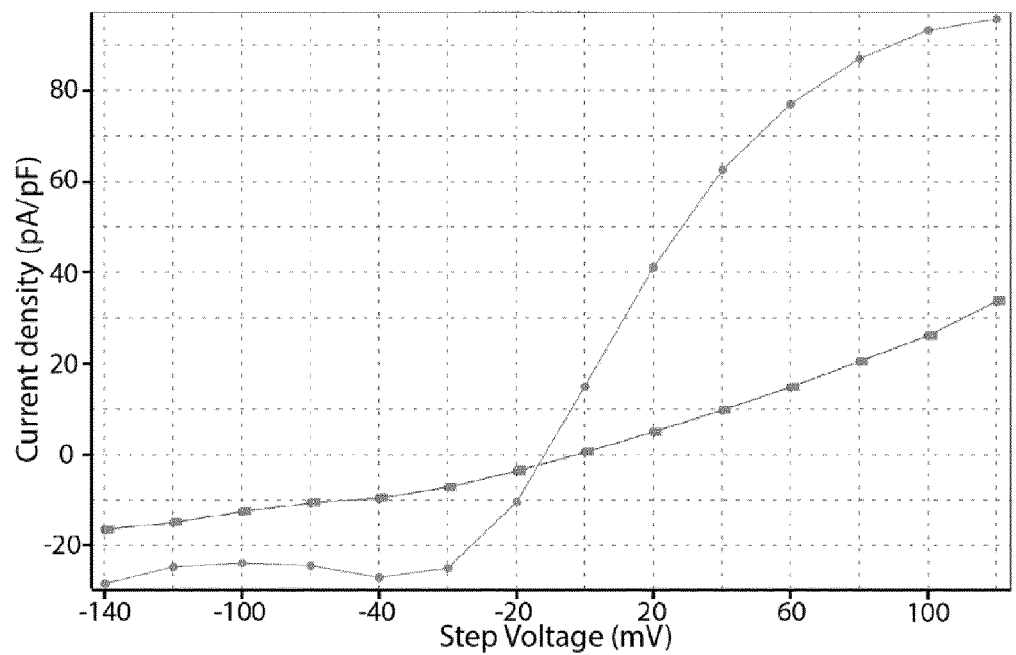
FIG. 2: Panel A shows a representative I/V plot of constant current density in a CIC-1 expressing CHO cell before (circles) and after (squares) application of 100 μM of the CIC-1 inhibitor, 9-anthracenecarboxylic acid (9-AC, Sigma A89405). Panel B shows a I/V plot of instant tail current density from the same CIC-1 expressing CHO cell as illustrated in Panel A, before (circles) and after (squares) application of 100 μM 9-AC.
Figure 2:
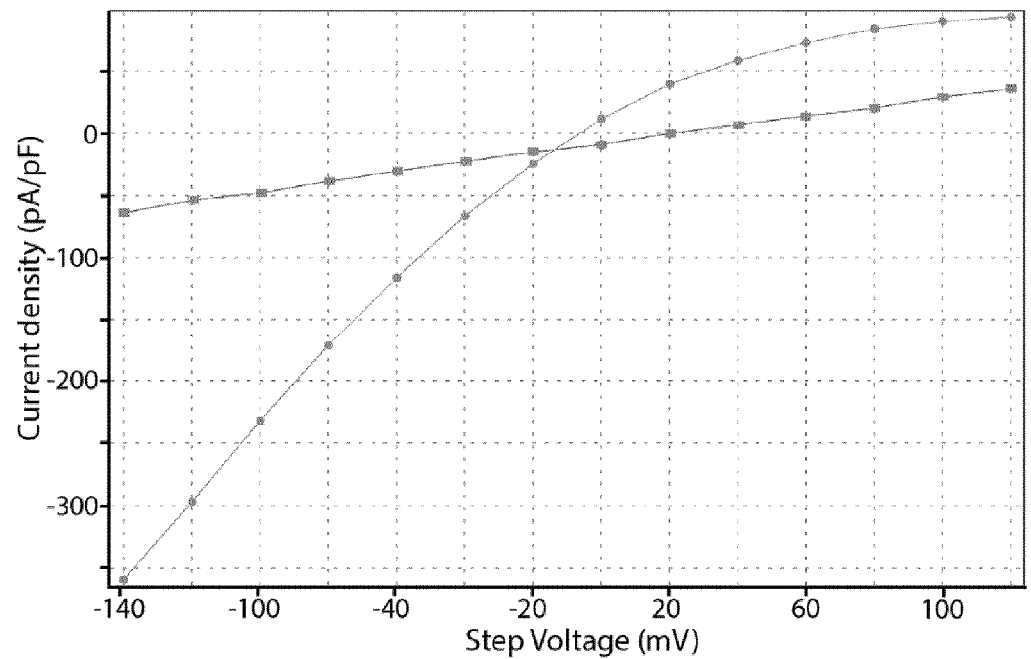

To evoke ClC-1 currents in whole cell patches, the membrane potential was initially stepped from a holding potential of −30 mV to +60 mV for 100 ms and then to various test voltages (sweeps) ranging from +120 mV to −140 mV in steps of 20 mV for 300 ms. To obtain tail currents, the membrane potential was stepped to −100 mV after each test voltage for 300 ms and then relaxed to −30 mV for 2 sec between sweeps (FIG. 1). I/V relationships for whole cell instant and steady state current amplitudes were obtained by plotting average current densities at the beginning and at the end of the 300 ms step against the membrane potential (FIG. 2).

Figure 3:
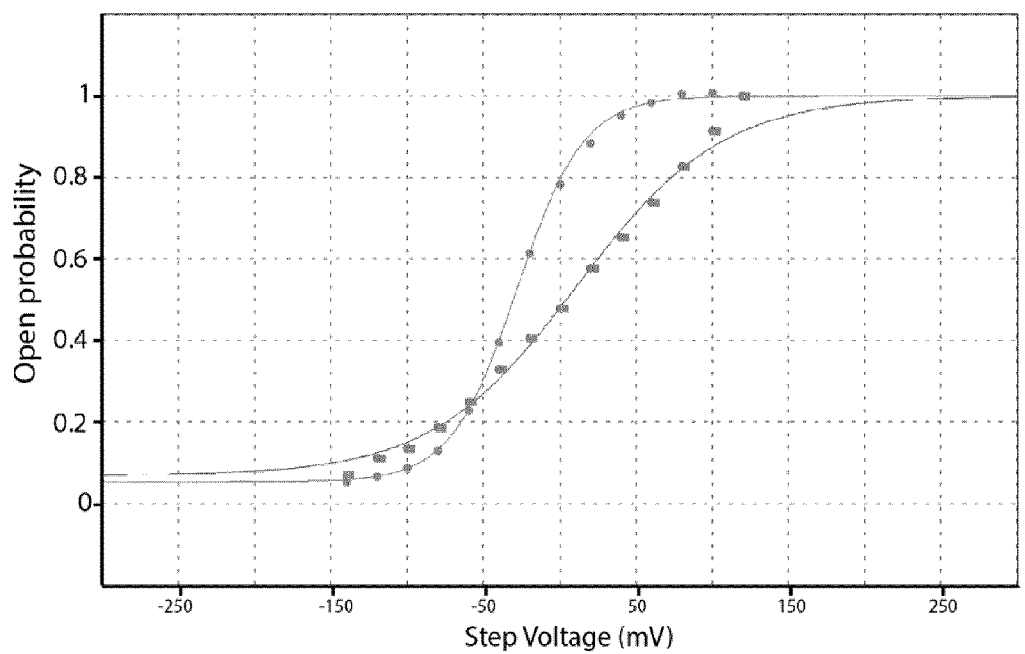
FIG. 3.

In order to determine the relative overall open probability ($P_O$), the instantaneous tail currents were normalized to the maximal tail current obtained following the most positive voltage step and plotted against the test voltage. Plots of normalized tail currents from each whole cell patch were then fitted to a Boltzmann function allowing determination of half activation voltages ($V_{1/2}$, FIG. 3).

Solutions

For automated patch clamp experiments extracellular solutions contained: 2 mM CaCl$_2$, 1 mM MgCl$_2$, 10 mM HEPES, 4 mM KCl, 145 mM NaCl, 10 mM Glucose, pH adjusted to 7.4 with NaOH (2 M). Osmolality adjusted to ~320 using sucrose.

Intracellular solutions contained: 80 mM CsF, 60 mM CsCl, 5/1 mM KOH/EGTA, 10 mM HEPES, 10 mM NaCl, pH adjusted to 7.2 with NaOH (2 M). Osmolality adjusted to ~320 mOsm using sucrose.

Cell Line Information

Cells used in patch clamp experiments were Chinese hamster ovary cells (CHO) constitutively expressing human ClC-1 channels. The amino acid sequence encoded by the cDNA used to create this cell line was identical to the translated sequence for GenBank accession number NM_000083.2. Cells were produced by Charles River (Catalogue CT6175, Cleveland OH, USA) in a cryopreserved format. Experiments were performed on the cells directly after thawing (3×10$^6$ cells used in each experiment).

Test Protocol

To evaluate the compound effect on ClC-1, when applied directly to the intracellular side of the cell membrane, the half activation voltage, $V_{1/2}$, was determined from whole cell patches with compound added to the intracellular solution and then compared to $V_{1/2}$ determined from control cell patches with only vehicle added to the intracellular solution. Additionally, the effect of extracellular added compound was evaluated by determine $V_{1/2}$ and steady state current amplitudes before and after exchanging the extracellular solution to contain compound.

The difference in half activation voltage of CIC-1 channels, $\Delta V_{1/2}$, was determined as the difference between the cell patches treated intracellularly with compound and control cells patches and is reported in Table 1 below. A positive shift in $\Delta V_{1/2}$ is reflecting CIC-1 channel inhibition by the tested compound. P-values of <0.05 is considered significant.

TABLE 1

Shift in half activation voltage, $V_{1/2}$

| Compound | $\Delta V1/2$ (mV) | P-value |
| --- | --- | --- |
| (2S)-2-(4-Bromo-2-(isoxazol-3-yl)phenoxy)propanoic acid | 14.1 | <0.01 |
| (2S)-2-[4-bromo-2-(1,2-oxazol-3-yl)phenoxy]butanoic acid | 7.2 | 0.01 |
| (2S)-2-[4-chloro-2-(1,2-oxazol-3-yl)phenoxy]propanoic acid | 8.1 | <0.01 |
| (2S)-2-[4-bromo-5-fluoro-2-(1,2-oxazol-3-yl)phenoxy]propanoic acid | 17.7 | <0.01 |
| 2-[4-bromo-2-(1,2-oxazol-3-yl)phenoxy]acetic acid | 11.3 | <0.01 |

Example 4: Measurement of In Situ Muscle Contractile Characteristics

Isometric hindlimb force was measured in 12-week old female Lewis rats in the presence and absence of compound.

Rats were placed under anesthesia with isoflurane (2-4%), intubated and subsequently connected to a micro ventilator (Microvent 1, Hallowell EMC, US). Two stimulation electrodes were inserted through the skin to stimulate the sciatic nerve. A small incision was made proximal to the ankle, to expose the Achilles tendon, which was tied by cotton string, and connected to a force transducer (Fort250, World Precision Instruments) with adjustable position (Vernier control). The Achilles tendon was then cut distal to the attached cotton string. The rat was placed on a heated pad, and to prevent movement artefacts from contraction of the ankle dorsiflexors, the foot was fixated by tape on a footplate.

Muscle contractile properties were assessed by applying an electrical current (under supramaximal voltage conditions) to the nerve and recording the force generated by the muscle. The muscle was stretched until maximal force was obtained, when assessed by 2 Hz stimulation. Isometric force was measured every 30 seconds at 12 Hz (Twitch), 10 pulses, and at every 5 minutes at 80 Hz (Tetanic) for 1 second (80 pulses). This stimulation pattern was employed throughout the experiment, except in a few cases where 80 Hz stimulation was replaced by 12 Hz (10 pulses). Neuromuscular transmission was partially inhibited by constant infusion of Cisatracurium (Nimbex, GlaxoSmithKline) at a concentration of 0.1 mg/kg at an adjustable infusion speed, adjusted individually for each animal to obtain a level of inhibition of ca. 50% of the forced generated at 12 Hz stimulation on the $4^{th}$ pulse. When the level of neuromuscular inhibition was stable, the test article was injected i.v. at the chosen concentration. The effect of test article was assessed on its ability to increase force generated from the stimulation pattern applied. The effect was assessed in the ability to increase force per se (tetanic, 80 Hz, stimulation), and the ratio between individual twitch peaks (12 Hz stimulation). The effect was monitored for at least 1 hour after injection of test article. In addition, the time from injection of test article to maximal effect on force (both twitch and tetanic) was noted and the time for the effect to disappear (return to baseline), if possible. When appropriate the infusion of neuromuscular blocking agent was ceased, with the stimulation pattern continued, and the return of force to control levels was monitored. Animals were sacrificed by cervical dislocation while still fully sedated.

(2S)-2-[4-bromo-5-fluoro-2-(1,2-oxazol-3-yl)phenoxy] propanoic acid was dosed 24.6 mg/kg i.v. The average increase in tetanic force was 46.2% (3 experiments). 2-[4-bromo-2-(1,2-oxazol-3-yl)phenoxy]acetic acid was dosed 44.8 mg/kg i.v. The average increase in tetanic force was 57.7% (2 experiments).

This demonstrates that compounds of the invention can restore force to muscles in vivo which have been partially inhibited by a neuromuscular blocker.

The invention claimed is:
1. A process for the preparation of compounds of Formula I

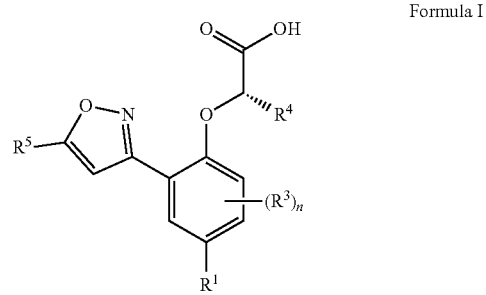

Formula I comprising step a) reacting
i) a compound of Formula II with an acid or base

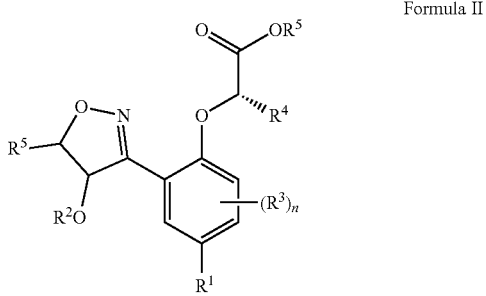

Formula II to form a reaction mixture and
ii) isolating a compound of Formula I from the reaction mixture,
wherein
$R^1$ is selected from the group consisting of H, F, Cl, Br and I;
$R^2$ is selected from the group consisting of C1-5 alkyl and C3-5 cycloalkyl;

$R^3$ is selected from the group consisting of deuterium, F, Cl, Br and I;

$R^4$ is selected from the group consisting of H, deuterium, C1-5 alkyl, C2-5 alkenyl, C2-5 alkynyl, C3-5 cycloalkyl and C5 cycloalkenyl, each of which may be optionally substituted with one or more, identical or different, substituents $R^7$;

$R^5$ is selected from the group consisting of C1-5 alkyl optionally substituted with one or more, identical or different, substituents $R^8$, C2-5 alkenyl, C2-5 alkynyl, C3-6 cycloalkyl optionally substituted with one or more, identical or different, substituents $R^8$, phenyl optionally substituted with one or more, identical or different, substituents $R^9$ and benzyl optionally substituted with one or more, identical or different, substituents $R^9$;

$R^6$ is selected from the group consisting of H, deuterium C1-5 alkyl and C3-5 cycloalkyl;

$R^7$ is independently selected from the group consisting of deuterium, tritium, F, Cl, Br, I, CN, isocyanide, C3-5 cycloalkyl optionally substituted with one or more, identical or different, substituents $R^8$, O—C1-3 alkyl optionally substituted with one or more, identical or different, substituents $R^8$, S—C1-3 alkyl optionally substituted with one or more, identical or different, substituents $R^8$, CH2-O—C1-3 alkyl optionally substituted with one or more, identical or different, substituents $R^8$; and CH2-S—C1-3 alkyl optionally substituted with one or more, identical or different, substituents $R^8$;

$R^8$ is independently selected from the group consisting of deuterium and F;

$R^9$ is independently selected from the group consisting of deuterium, methoxy, nitro, cyano, Cl, Br, I and F; and n is an integer 0, 1, 2 or 3.

2. The process of claim 1, wherein $R^1$ is Cl or Br.

3. The process of claim 1, wherein $R^2$ is C1-5 alkyl.

4. The process of claim 1, wherein $R^3$ is F.

5. The process of claim 1, wherein $R^4$ is C1-5 alkyl optionally substituted with one or more, identical or different, substituents $R^7$.

6. The process of claim 1, wherein $R^5$ is C1-5 alkyl optionally substituted with one or more, identical or different, substituents $R^8$.

7. The process of claim 1, wherein $R^6$ is H.

8. The process of claim 1, wherein n=0.

9. The process of claim 1, including reacting the compound of Formula II with an acid selected from the group consisting of formic acid, acetic acid, propionic acid, butyric acid, benzoic acid, hydrochloric acid and sulfuric acid or a mixture thereof.

10. The process of claim 1, wherein step a) i) is performed at a temperature of between 70° C. and 140° C.

11. The process of claim 1, wherein the reaction time of step a) i) is between 12 hours and 96 hours.

12. The process of claim 1, wherein the compound of Formula I is isolated from the reaction mixture in step a) ii) by adding water and extracting a product into an organic solvent.

13. The process of claim 1, wherein the compound of Formula I is an inhibitor of the ClC-1 chloride ion channel.

14. The process of claim 1, wherein the process further comprises step b)

i) Reacting a compound of Formula III

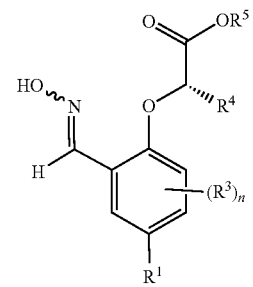

Formula III with N-chlorosuccinimide in an organic solvent to form a reaction mixture;

ii) adding a compound of Formula IV

Formula IV and a base to the reaction mixture; and iii) isolating a compound of Formula II from the reaction mixture, wherein $R^1$ to $R^9$ and n are as defined as in claim 1.

15. A compound selected from the group consisting of:

methyl (2S)-2-[4-bromo-2-(4-butoxy-4,5-dihydroisoxazol-3-yl)phenoxy]propanoate;

ethyl (2S)-2-[4-bromo-2-(4-butoxy-4,5-dihydroisoxazol-3-yl)phenoxy]propanoate;

tert-butyl (2S)-2-[4-bromo-2-(4-butoxy-4,5-dihydroisoxazol-3-yl) phenoxy]propanoate;

methyl (2S)-2-[4-bromo-2-(4-ethoxy-4,5-dihydroisoxazol-3-yl)phenoxy]propanoate;

ethyl (2S)-2-[4-bromo-2-(4-ethoxy-4,5-dihydroisoxazol-3-yl)phenoxy]propanoate;

tert-butyl (2S)-2-[4-bromo-2-(4-ethoxy-4,5-dihydroisoxazol-3-yl)phenoxy]propanoate;

methyl (2S)-2-[4-chloro-2-(5-cyclopropyl-4-butoxy-4,5-dihydroisoxazol-3-yl)phenoxy]propanoate;

methyl (2S)-2-[4-bromo-2-(5-methyl-4-butoxy-4,5-dihydroisoxazol-3-yl)phenoxy]propanoate;

methyl (2S)-2-[4-bromo-2-(5-cyclopropyl-4-butoxy-4,5-dihydroisoxazol-3-yl)phenoxy]propanoate;

ethyl (2S)-2-[4-chloro-2-(5-cyclopropyl-4-butoxy-4,5-dihydroisoxazol-3-yl)phenoxy]propanoate;

ethyl (2S)-2-[4-bromo-2-(5-methyl-4-butoxy-4,5-dihydroisoxazol-3-yl)phenoxy]propanoate, ethyl (2S)-2-[4-bromo-2-(5-cyclopropyl-4-butoxy-4,5-dihydroisoxazol-3-yl)phenoxy]propanoate;

tert-butyl (2S)-2-[4-chloro-2-(5-cyclopropyl-4-butoxy-4,5-dihydroisoxazol-3-yl)phenoxy]propanoate;

tert-butyl (2S)-2-[4-bromo-2-(5-methyl-4-butoxy-4,5-dihydroisoxazol-3-yl)phenoxy]propanoate;

tert-butyl (2S)-2-[4-bromo-2-(5-cyclopropyl-4-butoxy-4,5-dihydroisoxazol-3-yl)phenoxy]propanoate;

methyl (2S)-2-[4-chloro-2-(5-cyclopropyl-4-butoxy-4,5-dihydroisoxazol-3-yl)phenoxy]propanoate;

methyl (2S)-2-[4-bromo-2-(5-methyl-4-butoxy-4,5-dihydroisoxazol-3-yl)phenoxy]propanoate;
methyl (2S)-2-[4-bromo-2-(5-cyclopropyl-4-butoxy-4,5-dihydroisoxazol-3-yl)phenoxy]propanoate;
ethyl (2S)-2-[4-chloro-2-(5-cyclopropyl-4-butoxy-4,5-dihydroisoxazol-3-yl)phenoxy]propanoate;
ethyl (2S)-2-[4-bromo-2-(5-methyl-4-butoxy-4,5-dihydroisoxazol-3-yl)phenoxy]propanoate;
ethyl (2S)-2-[4-bromo-2-(5-cyclopropyl-4-butoxy-4,5-dihydroisoxazol-3-yl)phenoxy]propanoate;
tert-butyl (2S)-2-[4-chloro-2-(5-cyclopropyl-4-butoxy-4,5-dihydroisoxazol-3-yl)phenoxy]propanoate;
tert-butyl (2S)-2-[4-bromo-2-(5-methyl-4-butoxy-4,5-dihydroisoxazol-3-yl)phenoxy]propanoate;
tert-butyl (2S)-2-[4-bromo-2-(5-cyclopropyl-4-butoxy-4,5-dihydroisoxazol-3-yl)phenoxy]propanoate;
methyl (2S)-2-[4-bromo-5-fluoro-2-(4-butoxy-4,5-dihydroisoxazol-3-yl)phenoxy]-2-cyclopropylacetate;
methyl (2S)-2-[4-bromo-2-(4-butoxy-4,5-dihydroisoxazol-3-yl)phenoxy]-3-cyclobutylpropanoate;
methyl 2-[4-bromo-5-fluoro-2-(4-butoxy-4,5-dihydroisoxazol-3-yl)phenoxy]acetate;
methyl 2-[4-bromo-2-(4-butoxy-4,5-dihydroisoxazol-3-yl)phenoxy]acetate; methyl (2S)-2-[4,5-dichloro-2-(4-butoxy-4,5-dihydroisoxazol-3-yl)phenoxy]propanoate;
methyl (2S)-2-[4-bromo-5-fluoro-2-(4-butoxy-4,5-dihydroisoxazol-3-yl)phenoxy]propanoate;
methyl (2S)-2-[4-chloro-5-fluoro-2-(4-butoxy-4,5-dihydroisoxazol-3-yl)phenoxy]propanoate;
methyl (2S)-2-[4-chloro-2-(4-butoxy-4,5-dihydroisoxazol-3-yl)phenoxy]-3-cyclopropylpropanoate;
methyl (2S)-2-[4-fluoro-2-(4-butoxy-4,5-dihydroisoxazol-3-yl)phenoxy]propanoate;
methyl (2S)-2-[4-chloro-2-(4-butoxy-4,5-dihydroisoxazol-3-yl)phenoxy]-3-methylbutanoate;
methyl (2S)-2-[4-chloro-2-(4-butoxy-4,5-dihydroisoxazol-3-yl)phenoxy]butanoate;
methyl (2S)-2-[4-chloro-2-(4-butoxy-4,5-dihydroisoxazol-3-yl)phenoxy]propanoate;
methyl (2S)-2-[4-bromo-2-(4-butoxy-4,5-dihydroisoxazol-3-yl)phenoxy]-3-cyclopropylpropanoate;
methyl (2S)-2-[4-bromo-2-(4-butoxy-4,5-dihydroisoxazol-3-yl)phenoxy]butanoate;
methyl (2S)-2-[4-bromo-2-(4-butoxy-4,5-dihydroisoxazol-3-yl)phenoxy]-3-methylbutanoate;
methyl (2S)-2-[4-bromo-2-(4-butoxy-4,5-dihydroisoxazol-3-yl)phenoxy]propanoate;
ethyl (2S)-2-[4-bromo-5-fluoro-2-(4-butoxy-4,5-dihydroisoxazol-3-yl)phenoxy]-2-cyclopropylacetate;
ethyl (2S)-2-[4-bromo-2-(4-butoxy-4,5-dihydroisoxazol-3-yl)phenoxy]-3-cyclobutylpropanoate;
ethyl 2-[4-bromo-5-fluoro-2-(4-butoxy-4,5-dihydroisoxazol-3-yl)phenoxy]acetate;
ethyl 2-[4-bromo-2-(4-butoxy-4,5-dihydroisoxazol-3-yl)phenoxy]acetate; ethyl (2S)-2-[4,5-dichloro-2-(4-butoxy-4,5-dihydroisoxazol-3-yl)phenoxy]propanoate;
ethyl (2S)-2-[4-bromo-5-fluoro-2-(4-butoxy-4,5-dihydroisoxazol-3-yl)phenoxy]propanoate,
ethyl (2S)-2-[4-chloro-5-fluoro-2-(4-butoxy-4,5-dihydroisoxazol-3-yl)phenoxy]propanoate;
ethyl (2S)-2-[4-chloro-2-(4-butoxy-4,5-dihydroisoxazol-3-yl)phenoxy]-3-cyclopropylpropanoate;
ethyl (2S)-2-[4-fluoro-2-(4-butoxy-4,5-dihydroisoxazol-3-yl)phenoxy]propanoate;
ethyl (2S)-2-[4-chloro-2-(4-butoxy-4,5-dihydroisoxazol-3-yl)phenoxy]-3-methylbutanoate;
ethyl (2S)-2-[4-chloro-2-(4-butoxy-4,5-dihydroisoxazol-3-yl)phenoxy]butanoate;
ethyl (2S)-2-[4-chloro-2-(4-butoxy-4,5-dihydroisoxazol-3-yl)phenoxy]propanoate;
ethyl (2S)-2-[4-bromo-2-(4-butoxy-4,5-dihydroisoxazol-3-yl)phenoxy]-3-cyclopropylpropanoate;
ethyl (2S)-2-[4-bromo-2-(4-butoxy-4,5-dihydroisoxazol-3-yl)phenoxy]butanoate;
ethyl (2S)-2-[4-bromo-2-(4-butoxy-4,5-dihydroisoxazol-3-yl)phenoxy]-3-methylbutanoate;
ethyl (2S)-2-[4-bromo-2-(4-butoxy-4,5-dihydroisoxazol-3-yl)phenoxy]propanoate;
tert-butyl (2S)-2-[4-bromo-5-fluoro-2-(4-butoxy-4,5-dihydroisoxazol-3-yl)phenoxy]-2-cyclopropylacetate;
tert-butyl (2S)-2-[4-bromo-2-(4-butoxy-4,5-dihydroisoxazol-3-yl)phenoxy]-3-cyclobutylpropanoate;
tert-butyl 2-[4-bromo-5-fluoro-2-(4-butoxy-4,5-dihydroisoxazol-3-yl)phenoxy]acetate;
tert-butyl 2-[4-bromo-2-(4-butoxy-4,5-dihydroisoxazol-3-yl)phenoxy]acetate; tert-butyl (2S)-2-[4,5-dichloro-2-(4-butoxy-4,5-dihydroisoxazol-3-yl)phenoxy]propanoate;
tert-butyl (2S)-2-[4-bromo-5-fluoro-2-(4-butoxy-4,5-dihydroisoxazol-3-yl) phenoxy]propanoate;
tert-butyl (2S)-2-[4-chloro-5-fluoro-2-(4-butoxy-4,5-dihydroisoxazol-3-yl)phenoxy]propanoate;
tert-butyl (2S)-2-[4-chloro-2-(4-butoxy-4,5-dihydroisoxazol-3-yl)phenoxy]-3-cyclopropylpropanoate;
tert-butyl (2S)-2-[4-fluoro-2-(4-butoxy-4,5-dihydroisoxazol-3-yl)phenoxy]propanoate;
tert-butyl (2S)-2-[4-chloro-2-(4-butoxy-4,5-dihydroisoxazol-3-yl)phenoxy]-3-methylbutanoate;
tert-butyl (2S)-2-[4-chloro-2-(4-butoxy-4,5-dihydroisoxazol-3-yl)phenoxy]butanoate;
tert-butyl (2S)-2-[4-chloro-2-(4-butoxy-4,5-dihydroisoxazol-3-yl)phenoxy]propanoate,
tert-butyl (2S)-2-[4-bromo-2-(4-butoxy-4,5-dihydroisoxazol-3-yl)phenoxy]-3-cyclopropylpropanoate;
tert-butyl (2S)-2-[4-bromo-2-(4-butoxy-4,5-dihydroisoxazol-3-yl)phenoxy]butanoate;
tert-butyl (2S)-2-[4-bromo-2-(4-butoxy-4,5-dihydroisoxazol-3-yl)phenoxy]-3-methylbutanoate;
tert-butyl (2S)-2-[4-bromo-2-(4-butoxy-4,5-dihydroisoxazol-3-yl)phenoxy]propanoate;
methyl (2S)-2-[4-bro o-5-fluoro-2-(4-ethoxy-4,5-dihydroisoxazol-3-yl)phenoxy]-2-cyclopropylacetate;
methyl (2S)-2-[4-bromo-2-(4-ethoxy-4,5-dihydroisoxazol-3-yl)phenoxy]-3-cyclobutylpropanoate;
methyl 2-[4-bromo-5-fluoro-2-(4-ethoxy-4,5-dihydroisoxazol-3-yl)phenoxy]acetate;
methyl 2-[4-bromo-2-(4-ethoxy-4,5-dihydroisoxazol-3-yl)phenoxy]acetate; methyl (2S)-2-[4,5-dichloro-2-(4-ethoxy-4,5-dihydroisoxazol-3-yl)phenoxy]propanoate;
methyl (2S)-2-[4-bromo-5-fluoro-2-(4-ethoxy-4,5-dihydroisoxazol-3-yl)phenoxy]propanoate;
methyl (2S)-2-[4-chloro-5-fluoro-2-(4-ethoxy-4,5-dihydroisoxazol-3-yl)phenoxy]propanoate;
methyl (2S)-2-[4-chloro-2-(4-ethoxy-4,5-dihydroisoxazol-3-yl)phenoxy]-3-cyclopropylpropanoate;
methyl (2S)-2-[4-fluoro-2-(4-ethoxy-4,5-dihydroisoxazol-3-yl)phenoxy]propanoate;
methyl (2S)-2-[4-chloro-2-(4-ethoxy-4,5-dihydroisoxazol-3-yl)phenoxy]-3-methylbutanoate;
methyl (2S)-2-[4-chloro-2-(4-ethoxy-4,5-dihydroisoxazol-3-yl)phenoxy]butanoate;
methyl (2S)-2-[4-chloro-2-(4-ethoxy-4,5-dihydroisoxazol-3-yl)phenoxy]propanoate;

methyl (2S)-2-[4-bromo-2-(4-ethoxy-4,5-dihydroisoxazol-3-yl)phenoxy]-3-cyclopropylpropanoate;
methyl (2S)-2-[4-bromo-2-(4-ethoxy-4,5-dihydroisoxazol-3-yl)phenoxy]butanoate;
methyl (2S)-2-[4-bromo-2-(4-ethoxy-4,5-dihydroisoxazol-3-yl)phenoxy]-3-methylbutanoate;
methyl (2S)-2-[4-bromo-2-(4-ethoxy-4,5-dihydroisoxazol-3-yl)phenoxy]propanoate;
ethyl (2S)-2-[4-bromo-5-fluoro-2-(4-ethoxy-4,5-dihydroisoxazol-3-yl)phenoxy]-2-cyclopropylacetate;
ethyl (2S)-2-[4-bromo-2-(4-ethoxy-4,5-dihydroisoxazol-3-yl)phenoxy]-3-cyclobutylpropanoate;
ethyl 2-[4-bromo-5-fluoro-2-(4-ethoxy-4,5-dihydroisoxazol-3-yl)phenoxy]acetate;
ethyl 2-[4-bromo-2-(4-ethoxy-4,5-dihydroisoxazol-3-yl)phenoxy]acetate; ethyl (2S)-2-[4,5-dichloro-2-(4-ethoxy-4,5-dihydroisoxazol-3-yl)phenoxy]propanoate;
ethyl (2S)-2-[4-bromo-5-fluoro-2-(4-ethoxy-4,5-dihydroisoxazol-3-yl)phenoxy]propanoate;
ethyl (2S)-2-[4-chloro-5-fluoro-2-(4-ethoxy-4,5-dihydroisoxazol-3-yl)phenoxy]propanoate;
ethyl (2S)-2-[4-chloro-2-(4-ethoxy-4,5-dihydroisoxazol-3-yl)phenoxy]-3-cyclopropylpropanoate;
ethyl (2S)-2-[4-fluoro-2-(4-ethoxy-4,5-dihydroisoxazol-3-yl)phenoxy]propanoate;
ethyl (2S)-2-[4-chloro-2-(4-ethoxy-4,5-dihydroisoxazol-3-yl)phenoxy]-3-methylbutanoate;
ethyl (2S)-2-[4-chloro-2-(4-ethoxy-4,5-dihydroisoxazol-3-yl)phenoxy]butanoate;
ethyl (2S)-2-[4-chloro-2-(4-ethoxy-4,5-dihydroisoxazol-3-yl)phenoxy]propanoate;
ethyl (2S)-2-[4-bromo-2-(4-ethoxy-4,5-dihydroisoxazol-3-yl)phenoxy]-3-cyclopropylpropanoate,
ethyl (2S)-2-[4-bromo-2-(4-ethoxy-4,5-dihydroisoxazol-3-yl)phenoxy]butanoate;
ethyl (2S)-2-[4-bromo-2-(4-ethoxy-4,5-dihydroisoxazol-3-yl)phenoxy]-3-methylbutanoate;
ethyl (2S)-2-[4-bromo-2-(4-ethoxy-4,5-dihydroisoxazol-3-yl)phenoxy]propanoate;
tert-butyl (2S)-2-[4-bromo-S-fluoro-2-(4-ethoxy-4,5-dihydroisoxazol-3-yl)phenoxy]-2-cyclopropylacetate;
tert-butyl (2S)-2-[4-bromo-2-(4-ethoxy-4,5-dihydroisoxazol-3-yl)phenoxy]-3-cyclobutylpropanoate;
tert-butyl 2-[4-bromo-5-fluoro-2-(4-ethoxy-4,5-dihydroisoxazol-3-yl)phenoxy]acetate;
tert-butyl 2-[4-bromo-2-(4-ethoxy-4,5-dihydroisoxazol-3-yl)phenoxy]acetate; tert-butyl (2S)-2-[4,5-dichloro-2-(4-ethoxy-4,5-dihydroisoxazol-3-yl)phenoxy]propanoate;
tert-butyl (2S)-2-[4-bromo-5-fluoro-2-(4-ethoxy-4,5-dihydroisoxazol-3-yl)phenoxy]propanoate;
tert-butyl (2S)-2-[4-chloro-5-fluoro-2-(4-ethoxy-4,5-dihydroisoxazol-3-yl)phenoxy]propanoate;
tert-butyl (2S)-2-[4-chloro-2-(4-ethoxy-4,5-dihydroisoxazol-3-yl)phenoxy]-3-cyclopropylpropanoate;
tert-butyl (2S)-2-[4-fluoro-2-(4-ethoxy-4,5-dihydroisoxazol-3-yl)phenoxy]propanoate;
tert-butyl (2S)-2-[4-chloro-2-(4-ethoxy-4,5-dihydroisoxazol-3-yl)phenoxy]-3-methylbutanoate;
tert-butyl (2S)-2-[4-chloro-2-(4-ethoxy-4,5-dihydroisoxazol-3-yl)phenoxy]butanoate;
tert-butyl (2S)-2-[4-chloro-2-(4-ethoxy-4,5-dihydroisoxazol-3-yl)phenoxy]propanoate;
tert-butyl (2S)-2-[4-bromo-2-(4-ethoxy-4,5-dihydroisoxazol-3-yl)phenoxy]-3-cyclopropylpropanoate;
tert-butyl (2S)-2-[4-bromo-2-(4-ethoxy-4,5-dihydroisoxazol-3-yl)phenoxy]butanoate;
tert-butyl (2S)-2-[4-bromo-2-(4-ethoxy-4,5-dihydroisoxazol-3-yl)phenoxy]-3-methylbutanoate; and
tert-butyl (2S)-2-[4-bromo-2-(4-ethoxy-4,5-dihydroisoxazol-3-yl)phenoxy]propanoate.

16. A process for the preparation of a pharmaceutical composition comprising the steps of i) preparing a compound selected from the group consisting of (2S)-2-[4-bromo-5-fluoro-2-(1,2-oxazol-3-yl)phenoxy]-2-cyclopropylacetic acid; (2S)-2-[4-bromo-2-(1,2-oxazol-3-yl)phenoxy]-3-cyclobutylpropanoic acid; 2-[4-bromo-S-fluoro-2-(1,2-oxazol-3-yl)phenoxy]acetic acid, 2-[4-bromo-2-(1,2-oxazol-3-yl)phenoxy]acetic acid;

(2S)-2-[4,5-dichloro-2-(1,2-oxazol-3-yl)phenoxy]propanoic acid;

(2S)-2-[4-bromo-5-fluoro-2-(1,2-oxazol-3-yl)phenoxy]propanoic acid;

(2S)-2-[4-chloro-5-fluoro-2-(1,2-oxazol-3-yl)phenoxy]propanoic acid;

(2S)-2-[4-chloro-2-(1,2-oxazol-3-yl)phenoxy]-3-cyclopropylpropanoic acid; (2S)-2-[4-fluoro-2-(1,2-oxazol-3-yl)phenoxy]propanoic acid;

(2S)-2-[4-chloro-2-(5-cyclopropyl-1,2-oxazol-3-yl)phenoxy]propanoic acid;

(2S)-2-[4-chloro-2-(1,2-oxazol-3-yl)phenoxy]-3-methylbutanoic acid;

(2S)-2-[4-chloro-2-(1,2-oxazol-3-yl)phenoxy]butanoic acid;

(2S)-2-[4-chloro-2-(1,2-oxazol-3-yl)phenoxy]propanoic acid;

(2S)-2-[4-bromo-2-(1,2-oxazol-3-yl)phenoxy]-3-cyclopropylpropanoic acid; (2S)-2-[4-bromo-2-(1,2-oxazol-3-yl)phenoxy]butanoic acid;

(2S)-2-[4-bromo-2-(1,2-oxazol-3-yl)phenoxy]-3-methylbutanoic acid;

(2S)-2-[4-bromo-2-(5-methyl-1,2-oxazol-3-yl)phenoxy]propanoic acid;

(2S)-2-[4-bromo-2-(5-cyclopropyl-1,2-oxazol-3-yl)phenoxy]propanoic acid; and (2S)-2-[4-bromo-2-(1,2-oxazol-3-yl)phenoxy]propanoic acid, by a) reacting i) a compound of Formula II with an acid or base

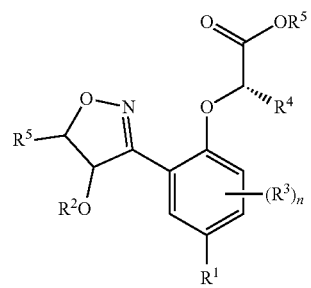

Formula II to form a reaction mixture and ii) isolating a compound of Formula I

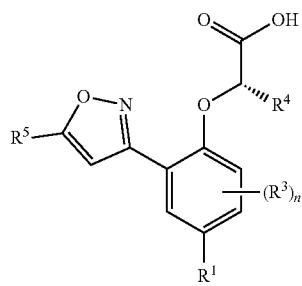

Formula I from the reaction mixture,
wherein
  $R^1$ is selected from the group consisting of H, F, Cl, Br and I;
  $R^2$ is selected from the group consisting of C1-5 alkyl and C3-5 cycloalkyl;
  $R^3$ is selected from the group consisting of deuterium, F, Cl, Br and I,
  $R^4$ is selected from the group consisting of H, deuterium, C1-5 alkyl, C2-5 alkenyl, C2-5 alkynyl, C3-5 cycloalkyl and C5 cycloalkenyl, each of which may be optionally substituted with one or more, identical or different, substituents $R^7$;
  $R^5$ is selected from the group consisting of C1-5 alkyl optionally substituted with one or more, identical or different, substituents $R^8$, C2-5 alkenyl, C2-5 alkynyl, C3-6 cycloalkyl optionally substituted with one or more, identical or different, substituents $R^8$, phenyl optionally substituted with one or more, identical or different, substituents $R^9$ and benzyl optionally substituted with one or more, identical or different, substituents $R^9$,
  $R^6$ is selected from the group consisting of H, deuterium C1-5 alkyl and C3-5 cycloalkyl;
  $R^7$ is independently selected from the group consisting of deuterium, tritium,
F, Cl, Br, I, CN, isocyanide, C3-5 cycloalkyl optionally substituted with one or more, identical or different, substituents $R^8$, O—C1-3 alkyl optionally substituted with one or more, identical or different, substituents $R^8$, S—C1-3 alkyl optionally substituted with one or more, identical or different, substituents $R^8$, CH2-O—C1-3 alkyl optionally substituted with one or more, identical or different, substituents $R^8$ and CH2-S—C1-3 alkyl optionally substituted with one or more, identical or different, substituents $R^8$;
  $R^8$ is independently selected from the group consisting of deuterium and F;
  $R^9$ is independently selected from the group consisting of deuterium,
methoxy, nitro, cyano, Cl, Br, I and F; and
n is an integer 0, 1, 2 or 3;
and
  ii) formulating said compound of Formula I into a pharmaceutical composition.

17. The process of claim 9 further including wherein the compound of Formula I is isolated from the reaction mixture in step a) ii) by adding water and extracting a product into an organic solvent.

18. The process of claim 17 further comprising step b)
  i) reacting a compound of Formula III

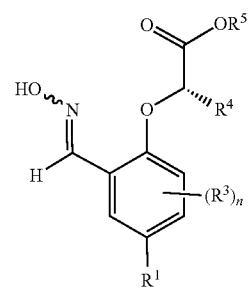

Formula III with N-chlorosuccinimide in an organic solvent to form a reaction mixture;
  ii) adding a compound of Formula IV

Formula IV and a base to the reaction mixture; and
  iii) isolating a compound of Formula II from the reaction mixture.

19. The process of claim 12 further comprising step b)
  i) reacting a compound of Formula III

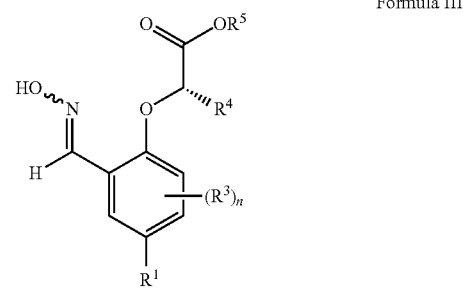

Formula III with N-chlorosuccinimide in an organic solvent to form a reaction mixture;
  ii) adding a compound of Formula IV

Formula IV and a base to the reaction mixture; and
  iii) isolating a compound of Formula II from the reaction mixture.

20. The process of claim 1 including wherein $R^2$ is C1-5 alkyl, $R^3$ is F, and $R^4$ is C1-5 alkyl optionally substituted with one or more, identical or different, substituents $R^7$.

21. The process of claim 1, wherein the compound of Formula II is reacted with a base.

22. The process of claim 1, wherein the compound of Formula I is purified by crystallisation from an organic solvent selected from the group consisting of toluene, ethyl acetate, isopropyl acetate, and tert-butyl methyl ether.

* * * * *